(12) United States Patent
Townsley et al.

(10) Patent No.: US 12,698,498 B2
(45) Date of Patent: *Aug. 4, 2026

(54) COMPOSITIONS AND METHODS FOR CONSTRUCTING STRAND SPECIFIC cDNA LIBRARIES

(71) Applicant: The Regents of the University of California, Oakland, CA (US)

(72) Inventors: Brad Townsley, Davis, CA (US); Michael F. Covington, Davis, CA (US); Neelima Sinha, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1092 days.

This patent is subject to a terminal disclaimer.

(21) Appl. No.: 17/667,841

(22) Filed: Feb. 9, 2022

(65) Prior Publication Data

US 2022/0389416 A1 Dec. 8, 2022

Related U.S. Application Data

(63) Continuation of application No. 15/569,568, filed as application No. PCT/US2016/030288 on Apr. 29, 2016, now Pat. No. 11,279,927.

(60) Provisional application No. 62/154,584, filed on Apr. 29, 2015.

(51) Int. Cl.

| | |
|---|---|
| *C12N 15/10* | (2006.01) |
| *C12P 19/34* | (2006.01) |
| *C12Q 1/6806* | (2018.01) |
| *C40B 40/08* | (2006.01) |

(52) U.S. Cl.
CPC .......... *C12N 15/1096* (2013.01); *C12P 19/34* (2013.01); *C12Q 1/6806* (2013.01); *C12Q 2521/107* (2013.01); *C12Q 2525/155* (2013.01); *C12Q 2525/179* (2013.01); *C12Q 2525/191* (2013.01); *C12Q 2535/122* (2013.01); *C12Q 2537/137* (2013.01); *C40B 40/08* (2013.01)

(58) Field of Classification Search
None
See application file for complete search history.

(56) References Cited

U.S. PATENT DOCUMENTS

| | | | |
|---|---|---|---|
| 8,183,359 B2 | 5/2012 | Becker et al. | |
| 2012/0156728 A1 | 6/2012 | Li et al. | |
| 2014/0274729 A1* | 9/2014 | Kurn ................... | B01J 19/0046 |
| | | | 506/26 |
| 2014/0274740 A1 | 9/2014 | Srinivasan et al. | |

FOREIGN PATENT DOCUMENTS

| | | |
|---|---|---|
| EP | 2746405 A1 | 6/2014 |
| WO | 98/40518 A2 | 9/1998 |
| WO | 2013/177220 A1 | 11/2013 |
| WO | 2014/096394 A1 | 6/2014 |
| WO | 2014/150435 A1 | 9/2014 |
| WO | 2014-150931 A1 | 9/2014 |

OTHER PUBLICATIONS

Agarwal, et al. "Sequencing of first-strand cDNA library reveals full-length transcriptomes." Nature communications 6 (2015): 6002.
Armour, et al. "Digital transcriptome profiling using selective hexamer priming for cDNA synthesis." Nature methods 6, No. 9 (2009): 647-649.
Smolina, et al. "End invasion of peptide nucleic acids (PNAs) with mixed-base composition into linear DNA duplexes." Nucleic acids research 33, No. 17 (2005): e146-e146.
Townsley, et al. "BrAD-seq: Breath Adapter Directional sequencing: a streamlined, ultra-simple and fast library preparation protocol for strand specific mRNA library construction." Frontiers in plant science 6 (2015).
International Search Report in PCT/US2016/030288, mailed Nov. 7, 2016.
Extended European Search Report in EP Application No. 16787282.9 mailed Aug. 16, 2018; 7 pages.
Ma, Z. et al.; "Isothermal amplification method for next-generation sequencing"; Proceedings of the National Academy of Sciences; vol. 110, No. 35; Aug. 27, 2013; pp. 14320-14323.
"Illumina TruSeq® Stranded mRNA kit" (User Guide (PN 15031047)) dated Oct. 2013.
Fei, J. et al.; "Watching DNA breath one molecule at a time"; PNAS; vol. 110, No. 43; Oct. 22, 2013; pp. 17173-17174.

* cited by examiner

*Primary Examiner* — Heather Calamita
*Assistant Examiner* — Jessica D Parisi
(74) *Attorney, Agent, or Firm* — Kilpatrick Townsend and Stockton LLP

(57) ABSTRACT

Provided herein are compositions, kits and methods for the production of strand-specific cDNA libraries. The compositions, kits and methods utilize properties of double stranded polynucleotides, such as RNA-cDNA duplexes to capture and incorporate a novel sequencing adapter. The methods are useful transcriptome profiling by massive parallel sequence, such as full-length RNA sequencing (RNA-Seq) and 3' tag digital gene expression (DGE).

13 Claims, 27 Drawing Sheets

Specification includes a Sequence Listing.

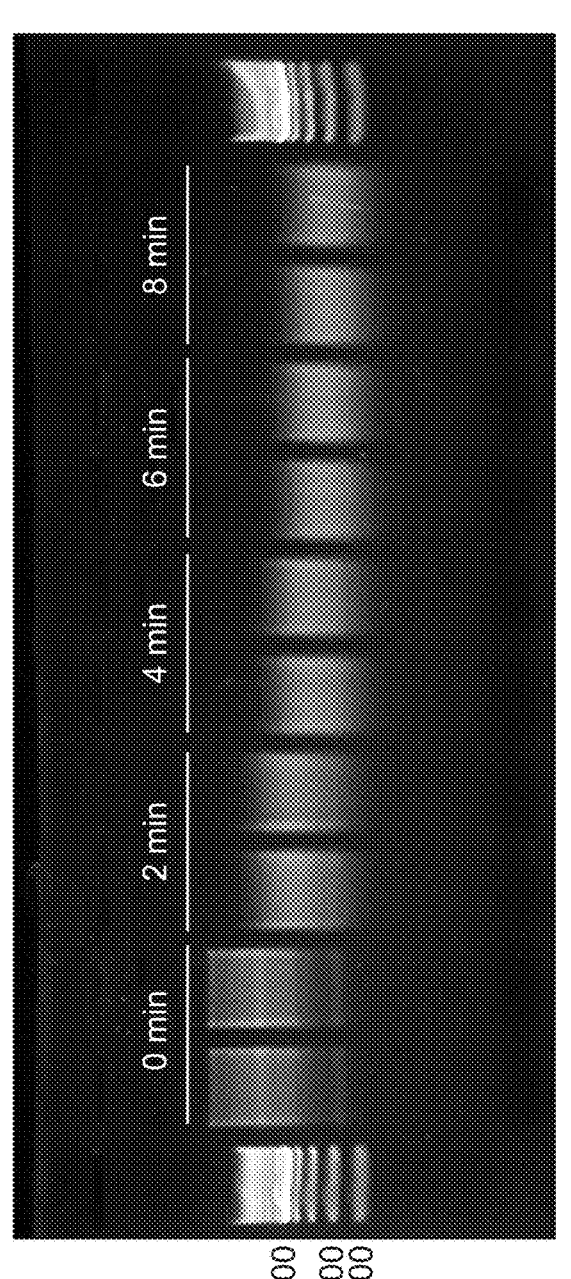
FIG. 7A
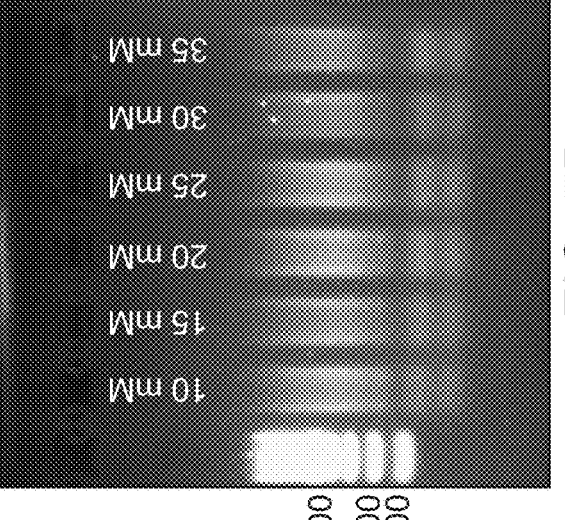
FIG. 7C
FIG. 7B

*FIG. 11A*
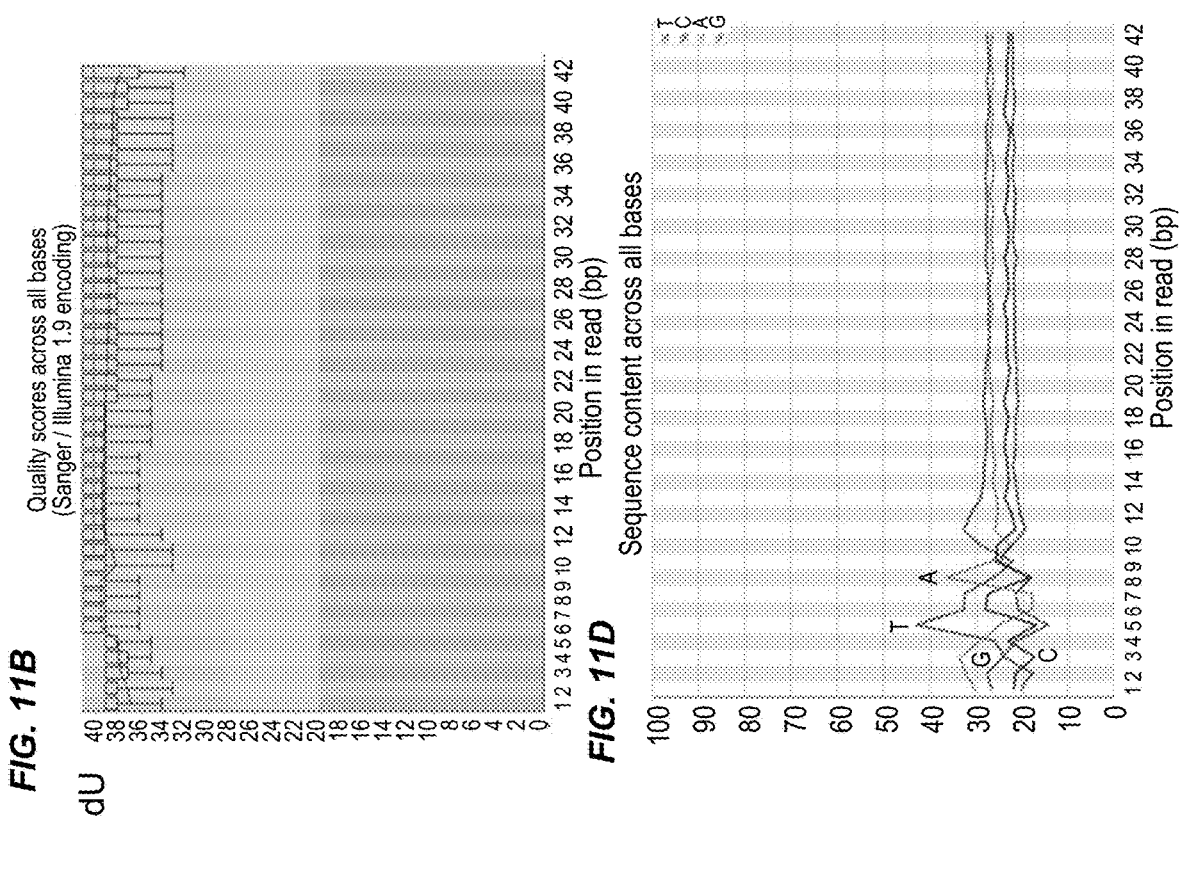
*FIG. 11B*
*FIG. 11C*
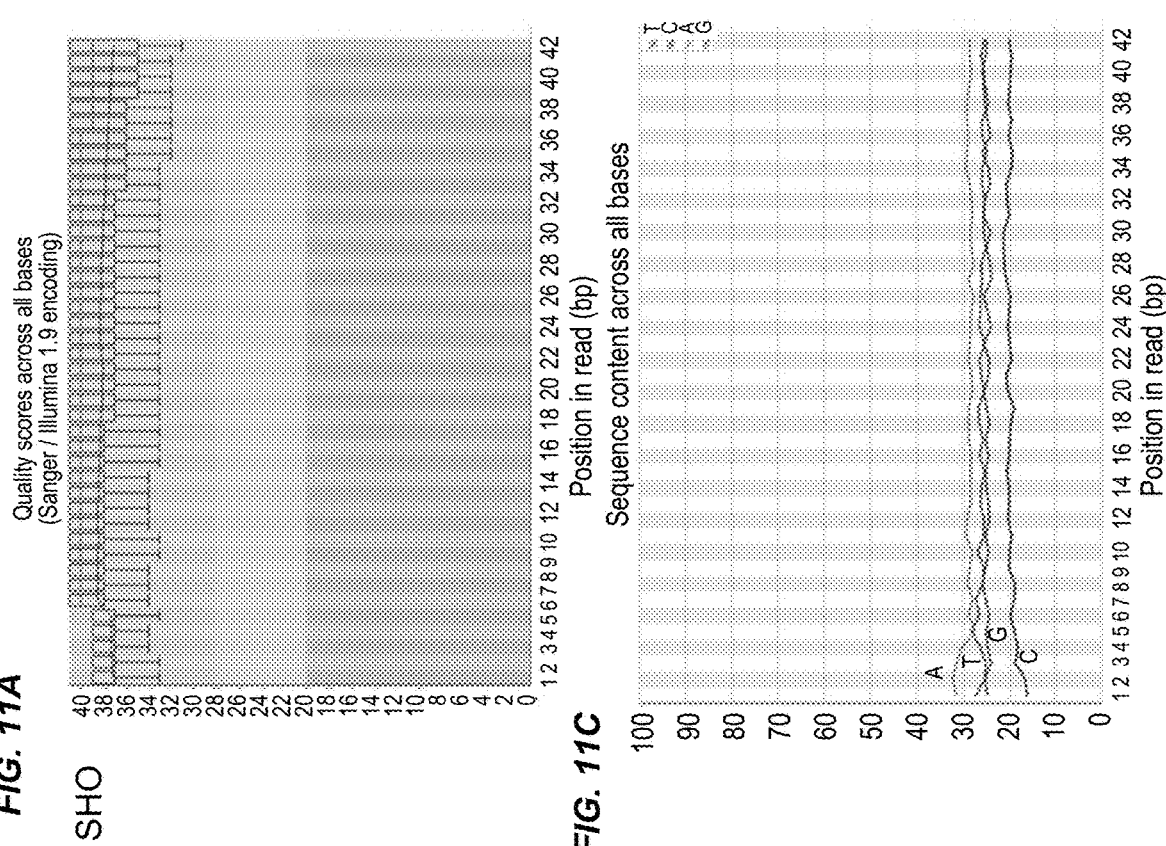
*FIG. 11D*

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
cctacacgac gctcttccga tct                                             23

<210> SEQ ID NO 2
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 2
agatcggaag agcgtcgtgt agg                                             23

<210> SEQ ID NO 3
<211> LENGTH: 35
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(29)
<223> OTHER INFORMATION: N = A, C, T or G
<220> FEATURE:
<221> NAME/KEY: misc_feature
<222> LOCATION: (30)..(35)
<223> OTHER INFORMATION: N may be present or absent; N = A, C, T or G

<400> SEQUENCE: 3
cctacacgac gctcttccga tctnnnnnn nnnnn                                 35

<210> SEQ ID NO 4
<211> LENGTH: 29
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(29)
<223> OTHER INFORMATION: N = A, C, T or G

<400> SEQUENCE: 4
cctacacgac gctcttccga tctnnnnnn                                       29

<210> SEQ ID NO 5
<211> LENGTH: 30
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(30)
<223> OTHER INFORMATION: N = A, C, T or G

<400> SEQUENCE: 5
cctacacgac gctcttccga tctnnnnnnn                                      30

-continued

```
<210> SEQ ID NO 6
<211> LENGTH: 31
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(31)
<223> OTHER INFORMATION: N = A, C, T or G

<400> SEQUENCE: 6
cctacacgac gctcttccga tctnnnnnnn n                                    31

<210> SEQ ID NO 7
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(32)
<223> OTHER INFORMATION: N = A, C, T or G

<400> SEQUENCE: 7
cctacacgac gctcttccga tctnnnnnnn nn                                   32

<210> SEQ ID NO 8
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(33)
<223> OTHER INFORMATION: N = A, C, T or G

<400> SEQUENCE: 8
cctacacgac gctcttccga tctnnnnnnn nnn                                  33

<210> SEQ ID NO 9
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(34)
<223> OTHER INFORMATION: N = A, C, T or G

<400> SEQUENCE: 9
cctacacgac gctcttccga tctnnnnnnn nnnn                                 34

<210> SEQ ID NO 10
<211> LENGTH: 35
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(35)
<223> OTHER INFORMATION: N = A, C, T or G

<400> SEQUENCE: 10
cctacacgac gctcttccga tctnnnnnnn nnnnn                                35
```

```
<210> SEQ ID NO 11
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: A is biotinylated

<400> SEQUENCE: 11
acaggacatt cgtcgcttcc tttttttttt tttttttttt                              40

<210> SEQ ID NO 12
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 12
gtgactggag ttcagacgtg tgctcttccg atcttttttt tttttttttt tttv            54

<210> SEQ ID NO 13
<211> LENGTH: 42
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (35)..(42)
<223> OTHER INFORMATION: N = A, C, T or G

<400> SEQUENCE: 13
gtgactggag ttcagacgtg tgctcttccg atctnnnnnn nn                          42

<210> SEQ ID NO 14
<211> LENGTH: 64
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (25)..(32)
<223> OTHER INFORMATION: N = A, C, T or G

<400> SEQUENCE: 14
caagcagaag acggcatacg agatnnnnnn nngtgactgg agttcagacg tgtgctcttc       60
cgat                                                                    64

<210> SEQ ID NO 15
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 15
aatgatacgg cgaccaccga gatctacact ctttccctac acgacgctct tccgatct        58

<210> SEQ ID NO 16
<211> LENGTH: 20
<212> TYPE: DNA
<213> ORGANISM: Artificial Sequence
```

-continued

```
<220> FEATURE:
<223> OTHER INFORMATION: synthetic oligonucleotide

<400> SEQUENCE: 16
aatgatacgg cgaccaccga                                                   20

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
caagcagaag acggcatacg a                                                 21

<210> SEQ ID NO 18
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 18
aaaaaaaaaa aaaaa                                                        15

<210> SEQ ID NO 19
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 19
tttttttttt tttttttv                                                    18

<210> SEQ ID NO 20
<211> LENGTH: 8
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(8)
<223> OTHER INFORMATION: N = A, C, T or G

<400> SEQUENCE: 20 nnnnnnnn                                                                8

<210> SEQ ID NO 21
<211> LENGTH: 8
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(8)
<223> OTHER INFORMATION: N = A, C, T or G

<400> SEQUENCE: 21 nnnnnnnn                                                                8

<210> SEQ ID NO 22
<211> LENGTH: 10
<212> TYPE: DNA
```

<213> ORGANISM: Artificial Sequence
<220> FEATURE:
<223> OTHER INFORMATION: synthetic oligonucleotide

<400> SEQUENCE: 22
ttgatatggg                                                                      10

<210> SEQ ID NO 23
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 23
ttgtgctggg                                                                      10

<210> SEQ ID NO 24
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 24
tacactaggg                                                                      10

<210> SEQ ID NO 25
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 25
tctgcctggg                                                                      10

<210> SEQ ID NO 26
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 26
tcaattaggg                                                                      10

<210> SEQ ID NO 27
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 27
tctctctggg                                                                      10

<210> SEQ ID NO 28
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 28
tgatactggg                                                                      10

-continued

```
<210> SEQ ID NO 29
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 29
tgccataggg                                                        10

<210> SEQ ID NO 30
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 30
tgtcaatggg                                                        10
```

COMPOSITIONS AND METHODS FOR CONSTRUCTING STRAND SPECIFIC cDNA LIBRARIES

CROSS-REFERENCES TO RELATED APPLICATIONS

This application is a continuation of U.S. application Ser. No. 15/569,568 filed Oct. 26, 2017, which is a U.S. National Stage of PCT/US2016/030288, International Filing Date Apr. 29, 2016, which claims priority to U.S. Provisional Application No. 62/154,584, filed Apr. 29, 2015, the disclosures of which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with Government support under Grant No. DBI1238243 Awarded by the National Science Foundation. The Government has certain rights in this invention.

REFERENCE TO SUBMISSION OF A SEQUENCE LISTING AS A TEXT FILE

The Sequence Listing written in file Sequence-1302118.txt created on Feb. 7, 2022, 7,567 bytes, machine format IBM-PC, MS-Windows operating system, is hereby incorporated by reference in its entirety for all purposes.

BACKGROUND OF THE INVENTION

Recent advances in high-throughput, next generation sequencing (NGS) technologies have enabled whole genome sequencing and new approaches to functional genomics, including comprehensive characterization and quantitation of any transcriptome. RNA-sequencing (RNA-Seq) involves direct sequencing of complementary DNA (cDNA) generated from messenger and structural RNAs and mapping the sequencing reads to a reference genome or gene set for gene expression analysis. This technique can be used to identify novel transcripts, small RNAs, alternative splicing products, fusion transcripts, sense transcripts and anti-sense transcripts. Another technique, known as Digital Gene Expression (DGE), utilizes NGS to determine the number of times a cDNA sequence is detected in a sample which is directly related that to the relative expression of RNA corresponding to the sequence.

One drawback of performing standard RNA-Seq is the lack of information on the direction of transcription. Stranded information identifies from which of the two DNA strands a target RNA transcript was derived. This information can provide, for example, increased confidence in transcript annotation, transcript discovery and expression profiling. Maintaining strand orientation also allows identification of antisense RNA expression, which is an important mediator of gene regulation. The ability to determine the level of sense and antisense expression provides more information into the transcriptome of a cell.

Methods have recently been developed for generating strand-specific RNA-Seq libraries. For example, one method marks one strand of either the original RNA (for example, by bisulfite treatment) or the transcribed cDNA (for example, by incorporation of modified nucleotides), followed by degradation of the unmarked strand. Unfortunately, these methods are labor intensive.

There remains a need for improved methods for generating directional (strand specific) cDNA libraries for performing RNA-Seq and digital gene expression (DGE) analysis using next generation sequencing.

BRIEF SUMMARY OF THE INVENTION

In one aspect, provided herein is a method of generating a strand specific cDNA molecule from an RNA molecule in an RNA sample. The method includes (a) isolating the RNA sample from a biological sample; (b) fragmenting the RNA molecule; (b) generating an RNA-complementary DNA (cDNA) duplex comprising the RNA molecule and a first cDNA strand by reverse transcription; (c) annealing a partially double stranded oligonucleotide 5' adapter to the 3' end of the first cDNA strand, wherein the 5' adapter comprises: (i) a first strand capturing oligonucleotide comprising at least 20 deoxyribonucleotides and a 3' overhang comprising about 6-12 consecutive random deoxyribonucleotides that anneal to the 3' end of the first cDNA strand; and (ii) a second strand blocking oligonucleotide comprising at least 20 deoxyribonucleotides complementary to at least a portion of the first strand capturing oligonucleotide; and (d) generating the strand specific cDNA molecule. In some embodiments, the method includes fragmenting the RNA molecule after step (a). In some instances, step (d) of generating the strand specific cDNA molecule includes extending the first strand capturing oligonucleotide of the 5' adapter using a DNA polymerase or a fragment thereof to generate a second cDNA strand complementary to the first cDNA strand. In some embodiments, the method also includes amplifying the second cDNA strand using a primer complementary to the second strand blocking oligonucleotide. The step of amplifying includes polymerase chain reaction (PCR).

In some embodiments, the method additionally includes determining the sequence of the amplified second cDNA strand. In some cases, the about 8-12 consecutive deoxyribonucleotides are substantially complementary to a preselected first cDNA strand. In other cases, the 8-12 consecutive deoxyribonucleotides are 100% complementary to a preselected first cDNA strand.

In some embodiments, the step of fragmenting the RNA sample is performed in a $Mg^{2+}$ containing buffer. The step (c) and/or (d) can be performed at room temperature.

In some instances, the DNA polymerase or fragment thereof is DNA polymerase I. In other instances, the DNA polymerase or fragment thereof is Klenow fragment.

In some embodiments, the second strand blocking oligonucleotide of the 5' adapter is 5' phosphorylated. In such cases, the DNA polymerase can be a Klenow fragment and a ligase.

The biological sample can be an animal tissue sample. Alternatively, the biological sample is a plant tissue sample.

In another aspect, provided herein is a kit comprising a partially double stranded oligonucleotide 5' adapter to the 3' end of the first cDNA strand, wherein the 5' adapter comprises: (i) a first strand capturing oligonucleotide comprising at least 20 deoxyribonucleotides and a 3' overhang comprising about 6-12 consecutive random deoxyribonucleotides that anneal to the 3' end of the first cDNA strand; and (ii) a second strand blocking oligonucleotide comprising at least 20 deoxyribonucleotides complementary to at least a portion of the first strand capturing oligonucleotide; a sequencing primer complementary to the second strand blocking oligo-nucleotide. Optionally, the kit can contain an instruction manual.

The first strand capturing oligonucleotide can include the sequence set forth in SEQ ID NO: 1. The second strand blocking oligonucleotide can include the sequence set forth in SEQ ID NO: 2. In some embodiments, the second strand blocking oligonucleotide is 5' phosphorylated.

The 3' overhang of the 5' adapter can be about 8-12 consecutive random deoxyribonucleotides. In some instances, the about 8-12 consecutive deoxyribonucleotides are substantially complementary to a preselected first cDNA strand of the RNA-cDNA duplex. In other instances, the about 8-12 consecutive deoxyribonucleotides are 100% complementary to a preselected first cDNA strand of the RNA-cDNA duplex.

In yet another aspect, provided herein is a polynucleotide complex. The polynucleotide complex comprises an RNA-cDNA duplex comprising an RNA molecule derived from a biological sample and a first cDNA strand generated by reverse transcription of the RNA molecule, and a partially double stranded oligonucleotide 5' adapter to the 3' end of the first cDNA strand, wherein the 5' adapter comprises: (i) a first strand capturing oligonucleotide comprising at least 20 deoxyribonucleotides and a 3' overhang comprising about 6-12 consecutive random deoxyribonucleotides that anneal to the 3' end of the first cDNA strand; and (ii) a second strand blocking oligonucleotide comprising at least 20 deoxyribonucleotides complementary to at least a portion of the first strand capturing oligonucleotide, wherein the 5' adapter anneals to the 3' end of the first cDNA strand of the RNA-cDNA duplex.

The first cDNA strand can be generated using a 3' adapter comprising a random nucleotide sequence. Alternatively, the first cDNA strand can be generated using a 3' adapter comprising a polyT sequence.

In some embodiments, the 3' overhang of the 5' adapter comprises about 8-12 consecutive random deoxyribonucle-otides. The about 8-12 consecutive deoxyribonucleotides may be substantially complementary to a preselected first cDNA strand of the RNA-cDNA duplex. In other cases, the about 8-12 consecutive deoxyribonucleotides may be 100% complementary to a preselected first cDNA strand of the RNA-cDNA duplex.

The first strand capturing oligonucleotide can include the sequence set forth in SEQ ID NO: 1. The second strand blocking oligonucleotide can include the sequence set forth in SEQ ID NO: 2.

Other objects, features, and advantages of the present invention will be apparent to one of skill in the art from the following detailed description and figures.

Figure 1:
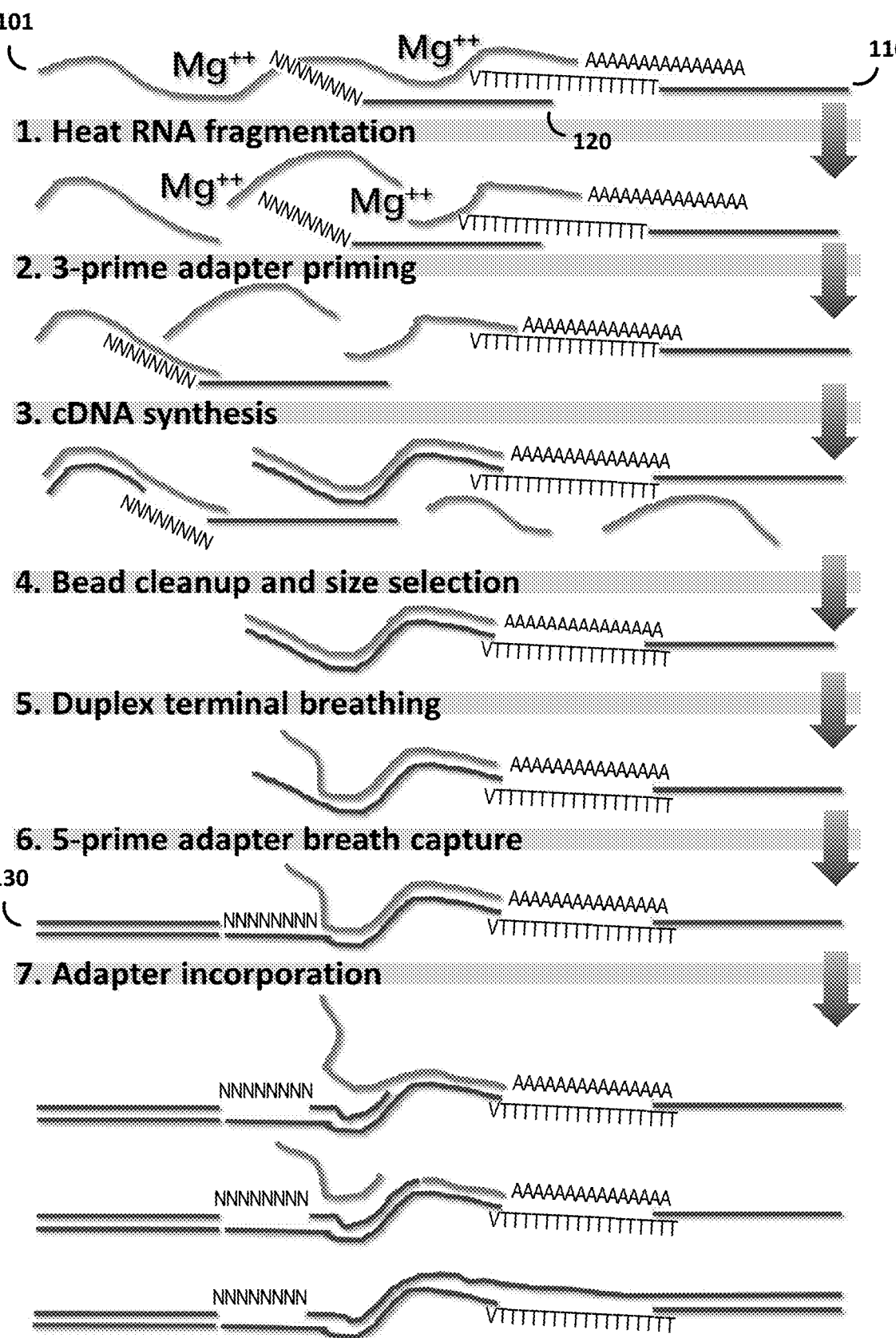
FIG. 1 shows a schematic diagram of strand-specific library synthesis mechanism. mRNAs (101) are fragmented by heat and magnesium (1) and primed for cDNA synthesis by an adapter-containing oligonucleotide (2 and 3). The exemplary mRNA transcript includes a poly A tail (SEQ ID NO:18; 5'-AAAAAAAAAAAAAAAA). The exemplary DGE primer contains the nucleic acid sequence of SEQ ID NO:19 (5'-TTTTTTTTTTTTTTTTTTTV). The exemplary SHO primer includes the nucleic acid sequence of SEQ ID NO:20 (5'-NNNNNNNN).

Size selection and cleanup removes unincorporated oli-gonucleotides and small cDNA fragments (4). Transient duplex breathing at the terminus of the RNA-cDNA hybrid (5) facilitates interaction with the single-stranded portion of the 5-prime capturing adapter (6) and *E. coli* DNA Poly-merase I catalyzes its incorporation into a complete library molecule (7). The exemplary double-stranded 5'-adapter (130) is shown with an overhang of 8 random deoxyribo-nucleotides (SEQ ID NO:21; 5'-NNNNNNNN).

Figure 2A:
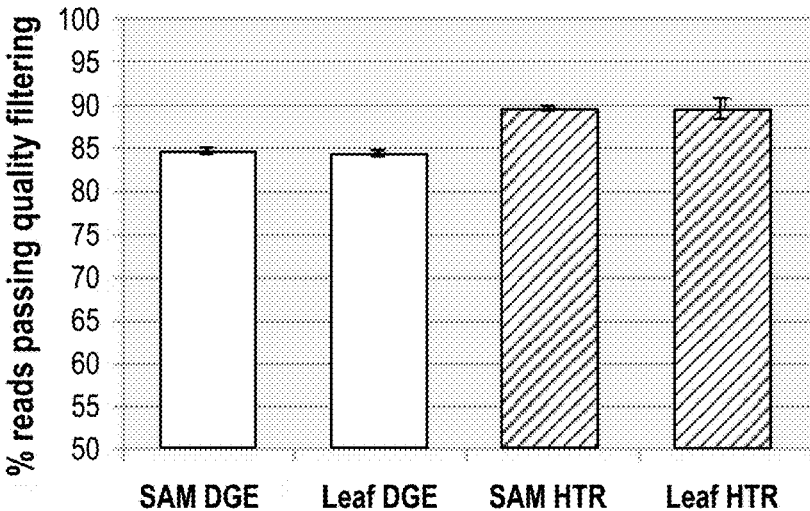
Figure 2B:
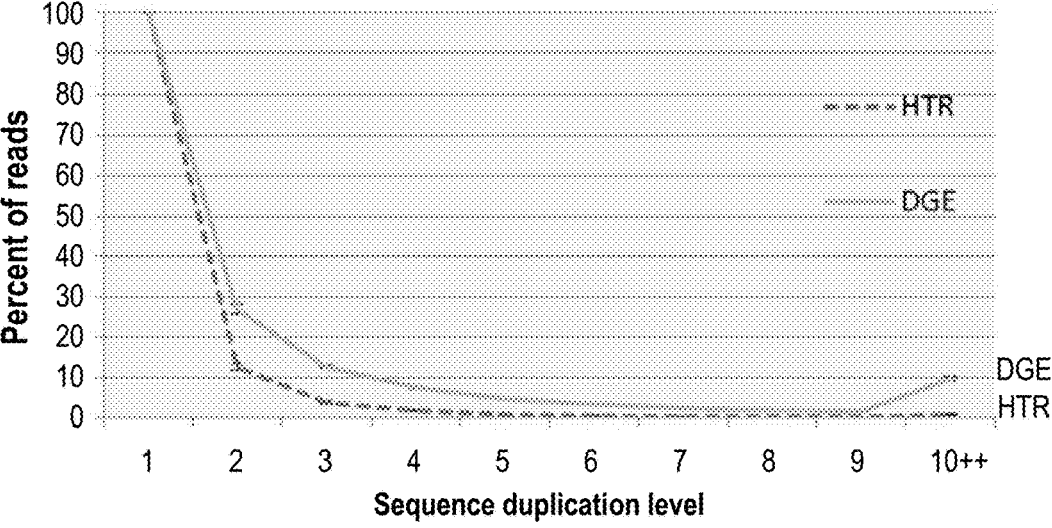
Figure 2C:
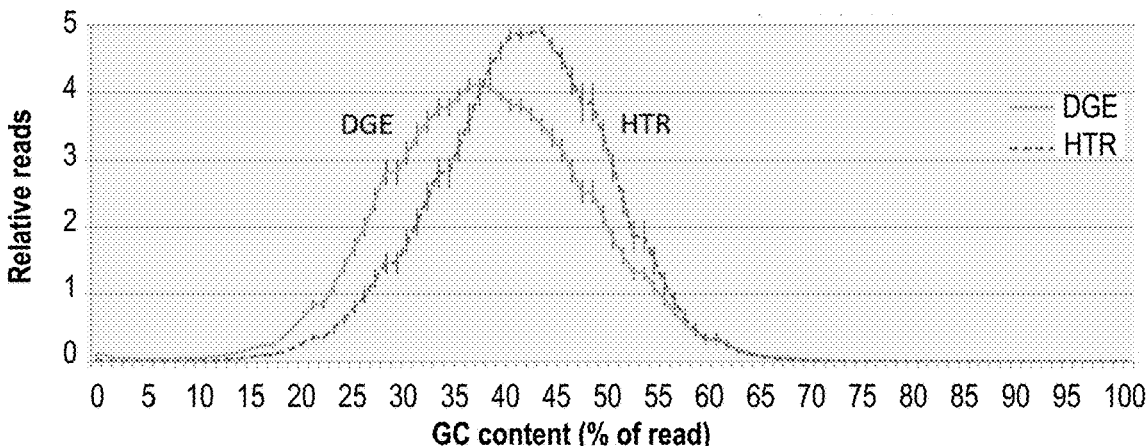
Figure 2D:
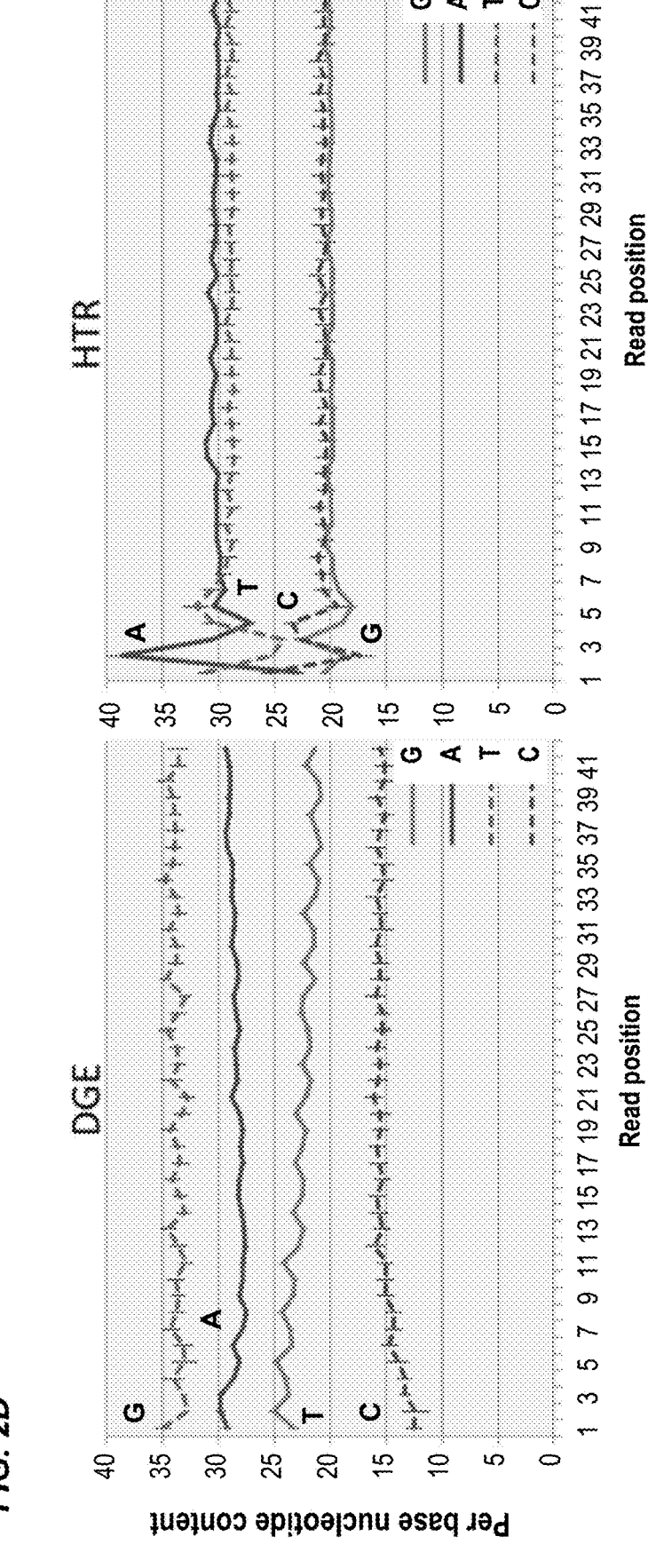

FIG. 2A-2D provide analysis of library quality and char-acteristics. Percentage of reads passing all quality filtering steps (FIG. 2A). Sequence duplication levels for DGE and HTR (FIG. 2B). GC content of reads in DGE and HTR (FIG. 2C). The average GC content is lower and the distribution broader in DGE than HTR. The composition of individual nucleotides differs between the strand-specific DGE and non-strand-specific HTR libraries (FIG. 2D). Sequence bias is more evident in the HTR libraries in the first several positions of the trimmed quality-filtered reads. Error bars reflect standard deviation among samples separated by tissue and method (FIG. 2A) or by method (FIGS. 2B and 2C)

Figure 3A:
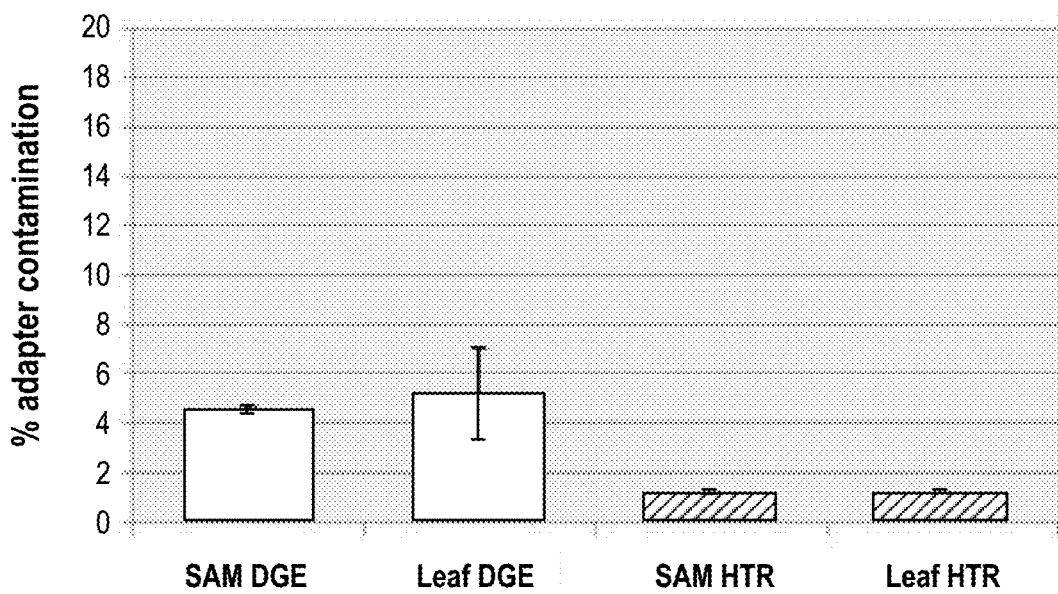
Figure 3B:
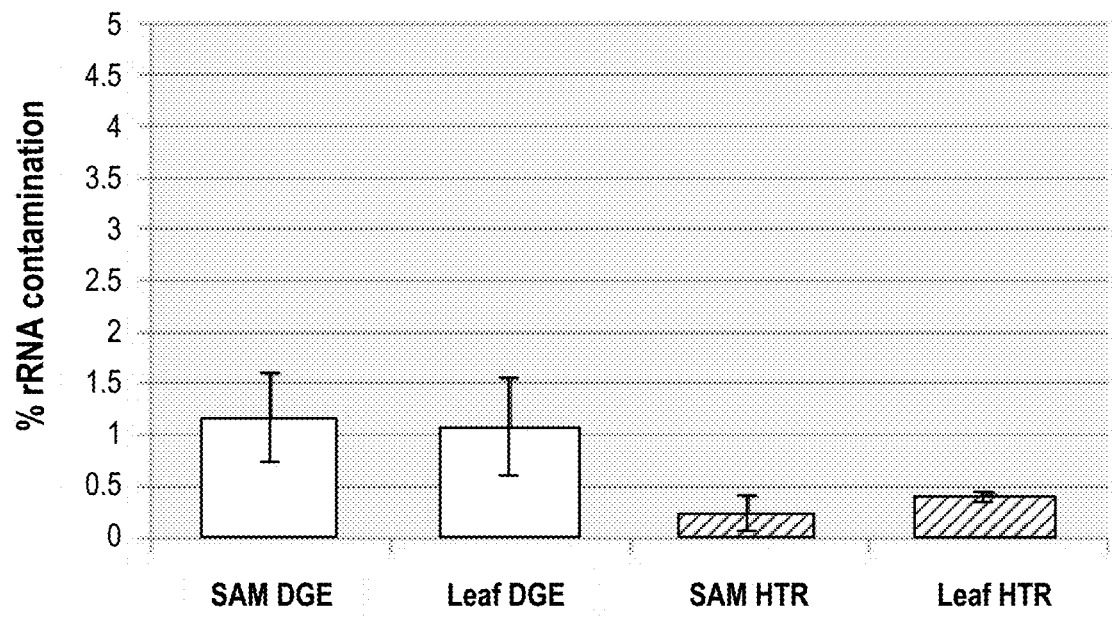
Figure 3C:
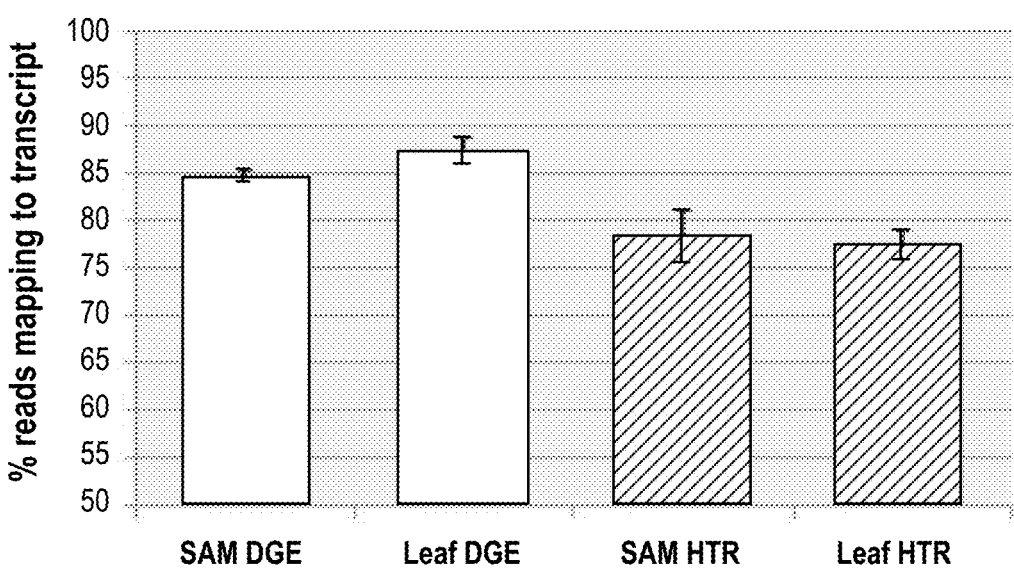
Figure 3D:
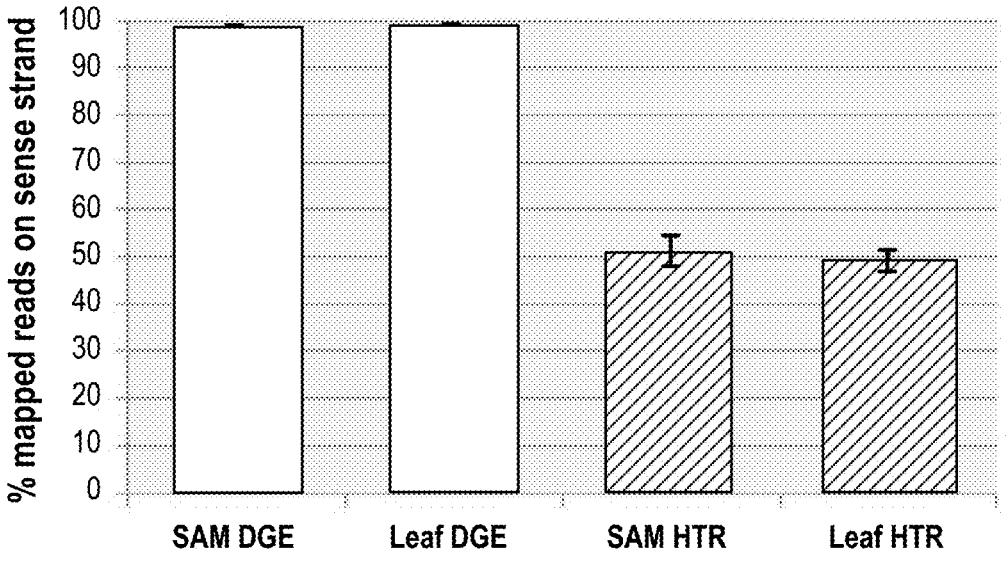

FIGS. 3A-3D provide read mapping and strand specific-ity. Fraction of reads coming from adapter (FIG. 3A) and ribosomal RNA (FIG. 3B) contamination. Reads mapping to either strand of ITAGcds+500 reference (FIG. 3C). Coding sequence mapped reads belonging to plus strand (FIG. 3D).

Figures 4A, 4B:
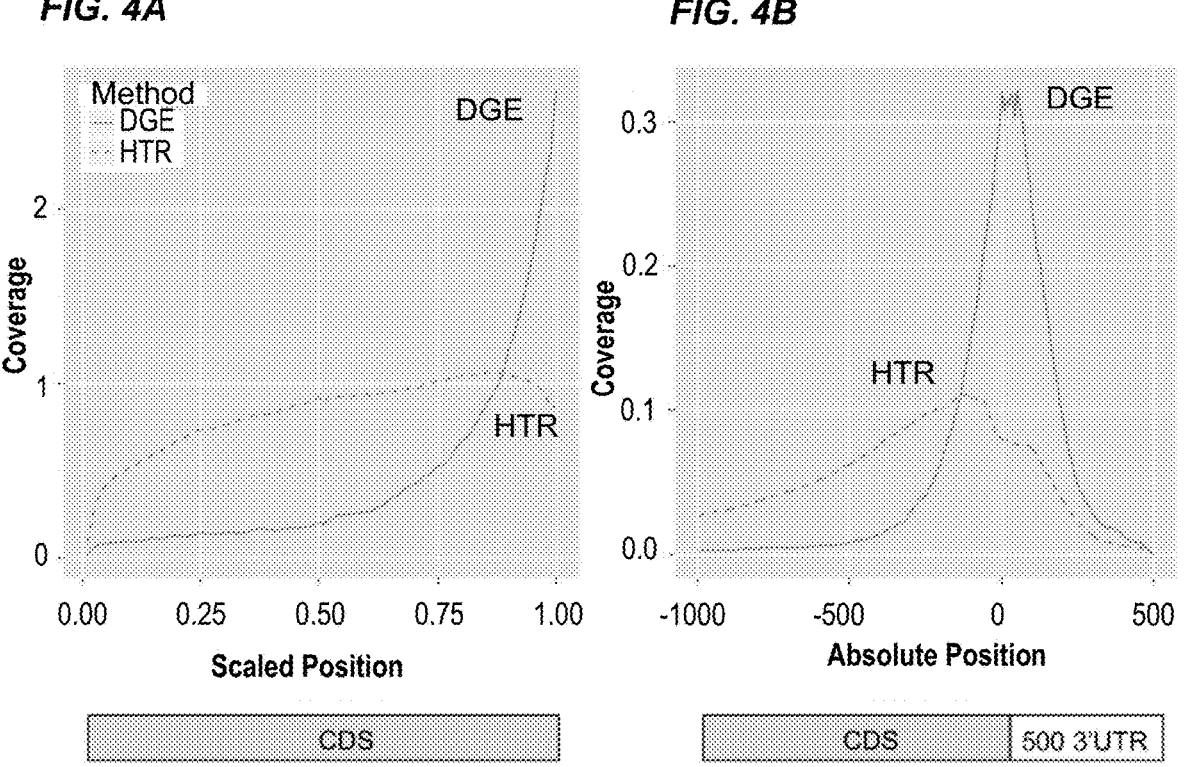
Figure 4C:
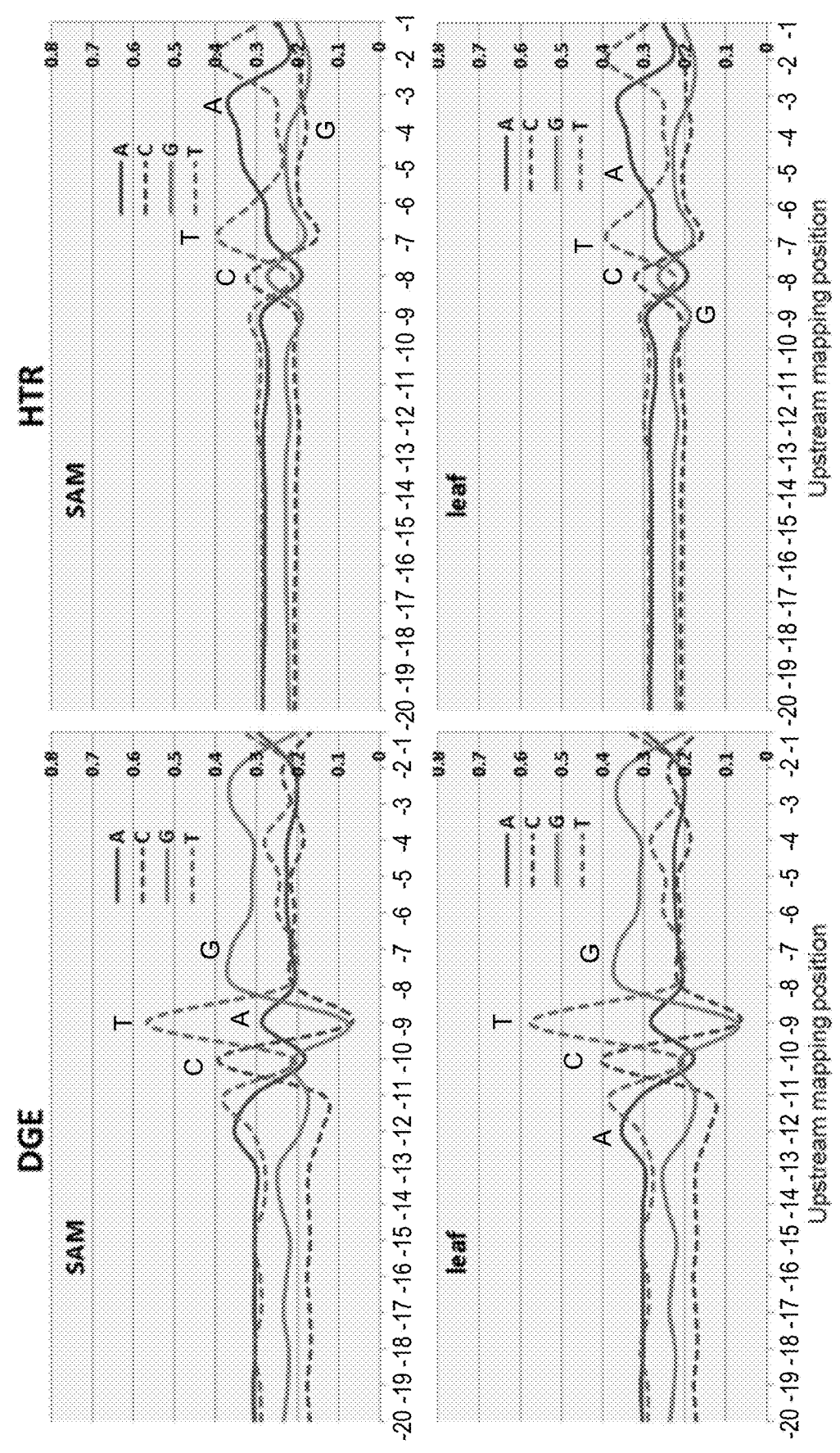
Figures 5A, 5B, 5C, 5D:
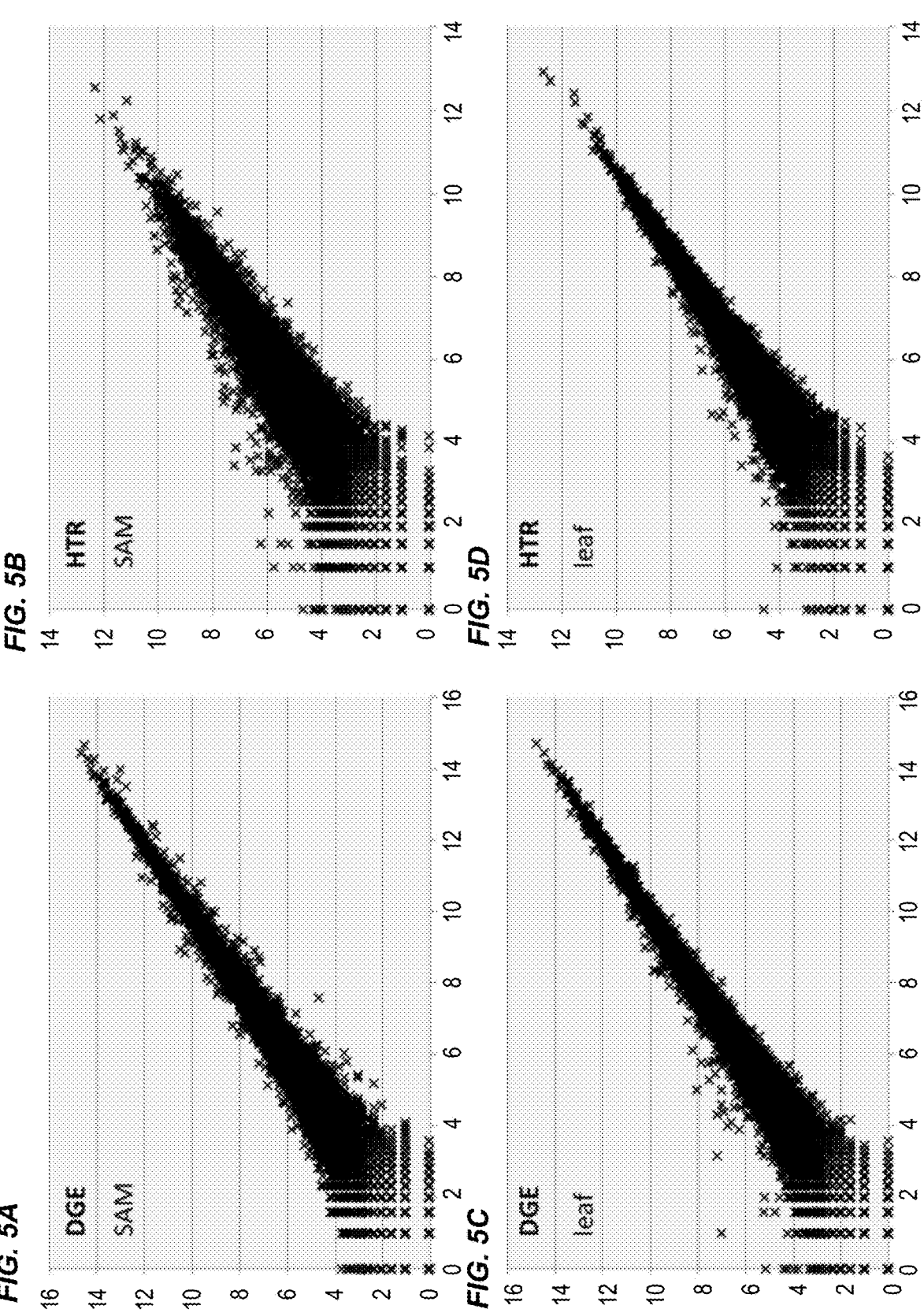

FIGS. 4A-4C show transcript coverage and cDNA sequence selection bias. Localization of DGE and HTR reads within the mapping reference (FIG. 4A), DGE reads mapped to 1.5 KB window localize near the annotated stop codon. Base frequencies for transcript nucleotides upstream of mapped reads (FIGS. 4B and 4C).

FIGS. 5A-5D show log 2-transformed expression corre-lations for representative sample pairs for each sample DGE and HTR using a representative pair of samples for each. Mean R-squared values for all DGE and HTR.

Figures 6A, 6B:
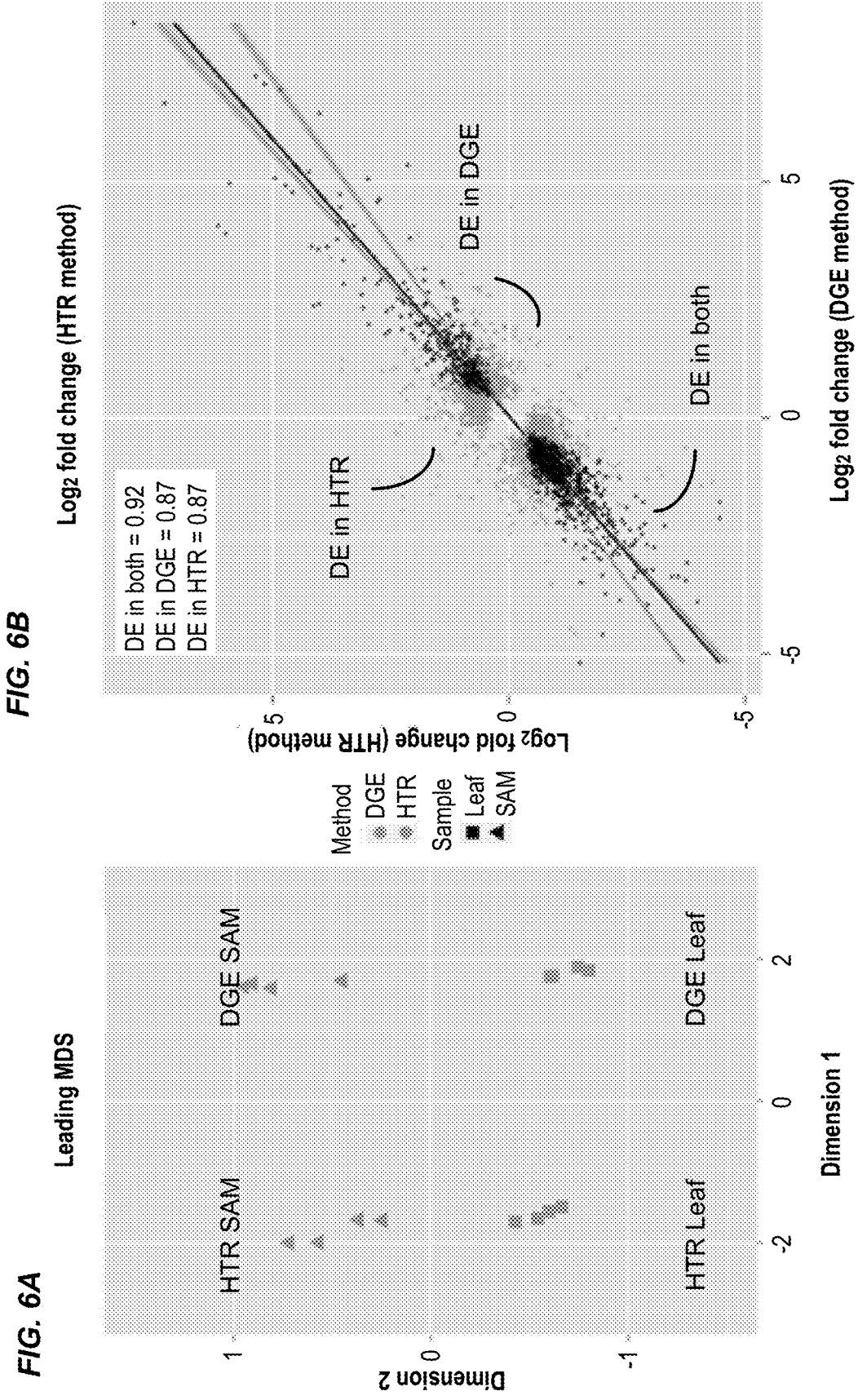

FIGS. 6A-6B show Multi-Dimensional Scaling (MDS) plot for DGE and HTR. SAM and Leaf samples (FIG. 6A). SAM vs. Leaf $Log_2$ fold change comparison between DGE and HTR (FIG. 6B).

FIGS. 7A-7C depict RNA fragmentation by 3 mM mag-nesium at 94° C. at increasing time intervals (FIG. 7A). Effect on library output of MgCl concentration in breath capture reaction using *E. coli* Polymerase I (FIG. 7B). Breath capture reaction is successfully facilitated by *E. coli* polymerase I (2.5 U), Klenow fragment (1.25 U) and Kle-now exo-(1.25 U) (FIG. 7C). Lanes shown in FIG. 7C are 4, 2 and 2 technical replicates respectively. Breath capture reactions (FIGS. 7B and 7C) were carried out at room temperature for 15 minutes.

Figure 8:
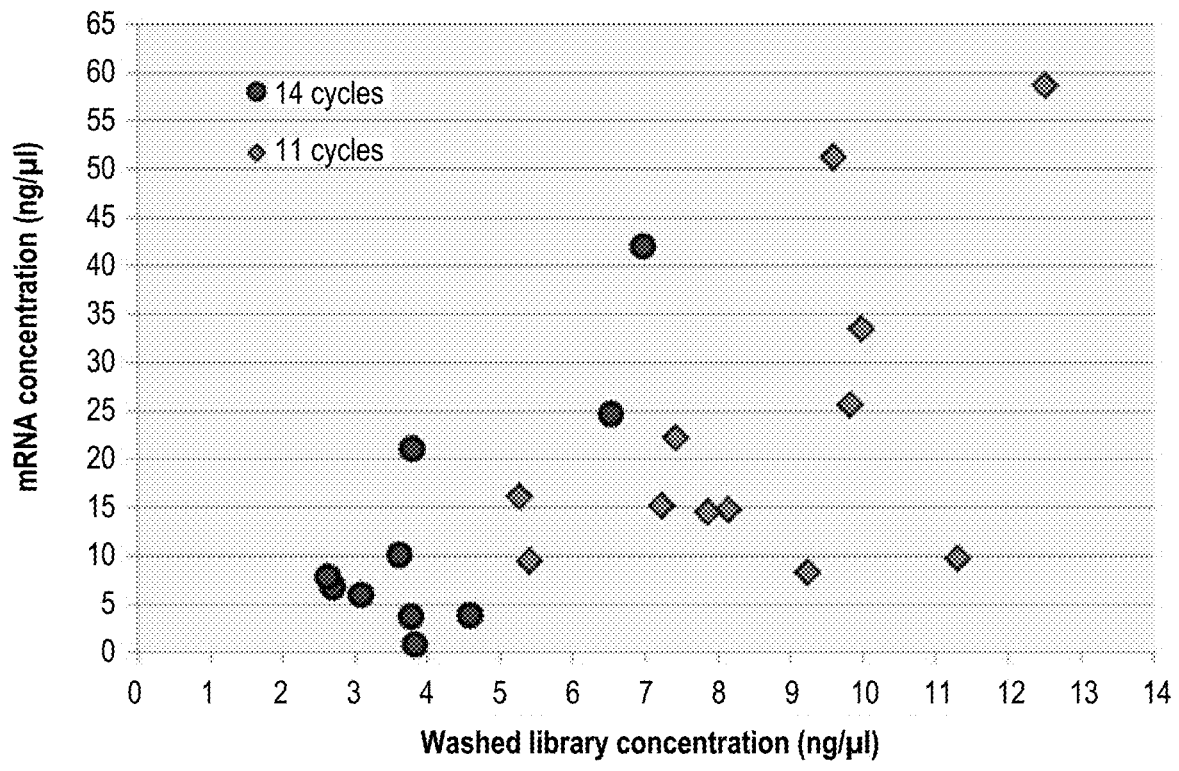

FIG. 8 shows RNA starting amounts vs library amplifi-cation, number cycles used and concentration of washed libraries prior to pooling.

Figure 9A:
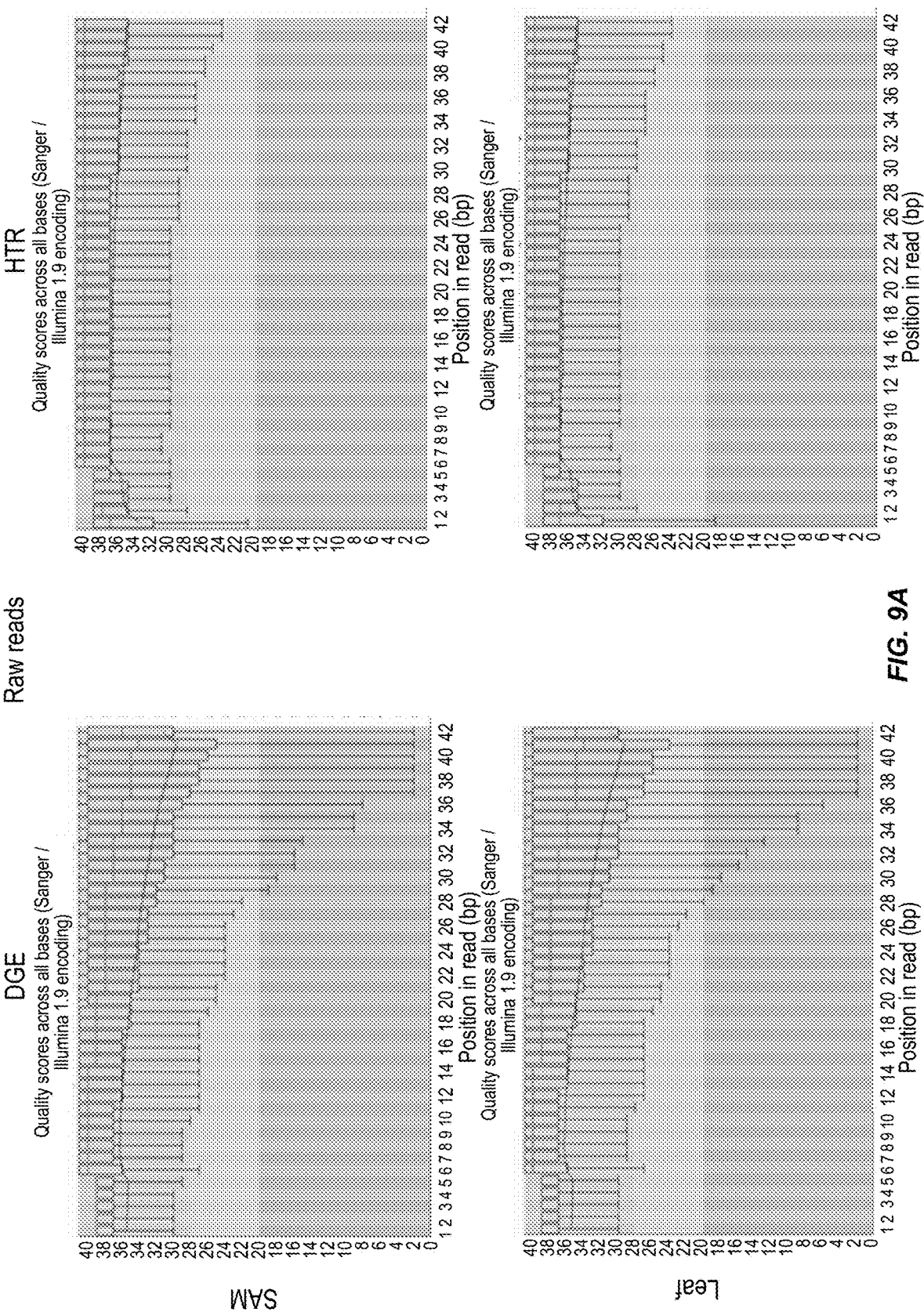
Figure 9B:
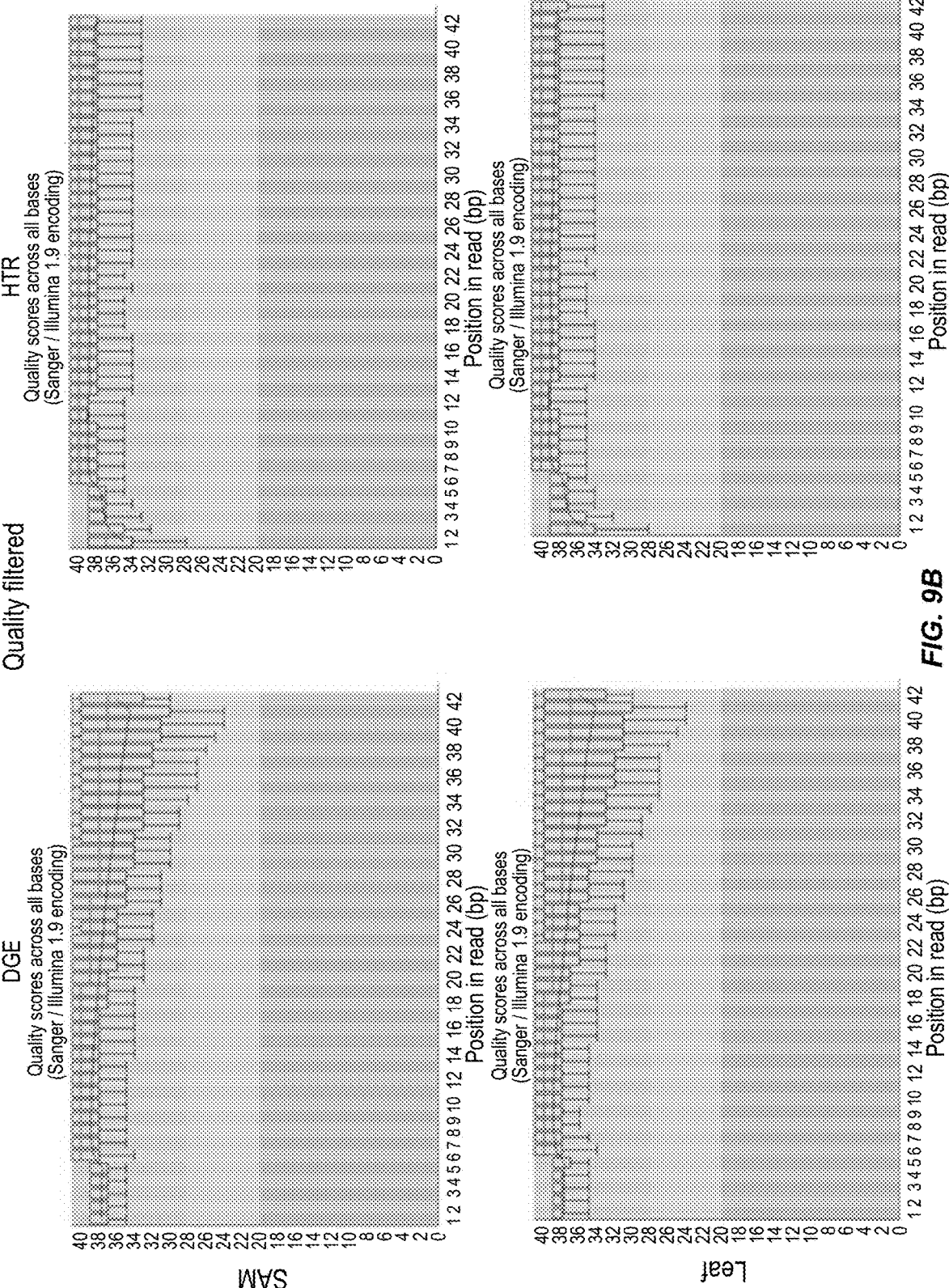

FIGS. 9A-9B shows pre and post quality filtering PHRED scores for DGE and HTR libraries used in this study.

Figure 10:
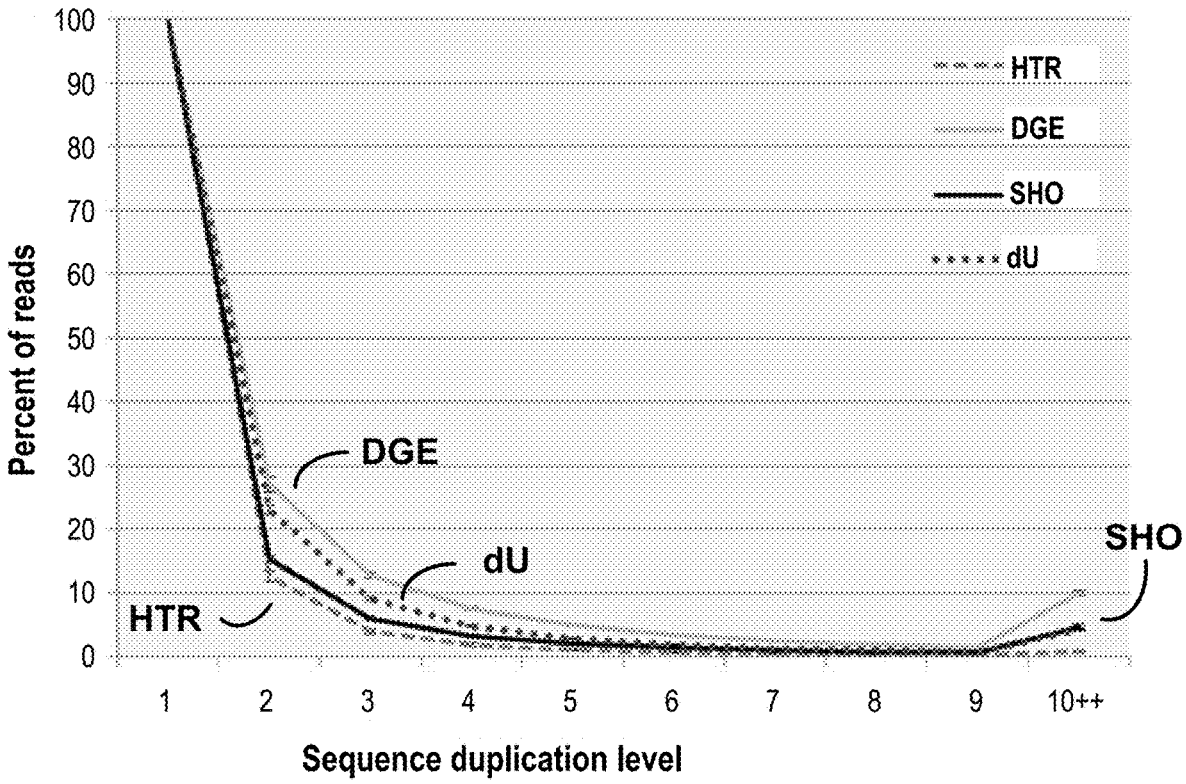

FIG. 10 shows sequence duplication rates per million quality filtered reads. High throughput HTR 23.12% (dashed), DGE 66.15% (solid), Shotgun (SHO) 53.63% (solid), deoxy-Uracil marked (dU) 48.28% (dotted)

Figure 11E:
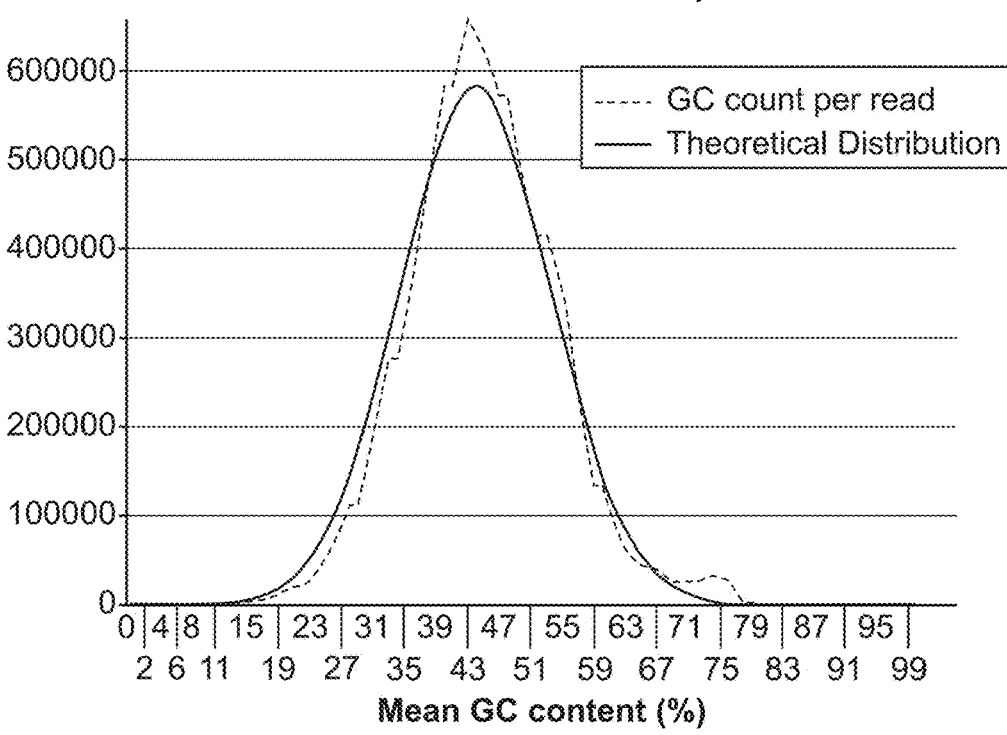
Figure 11F:
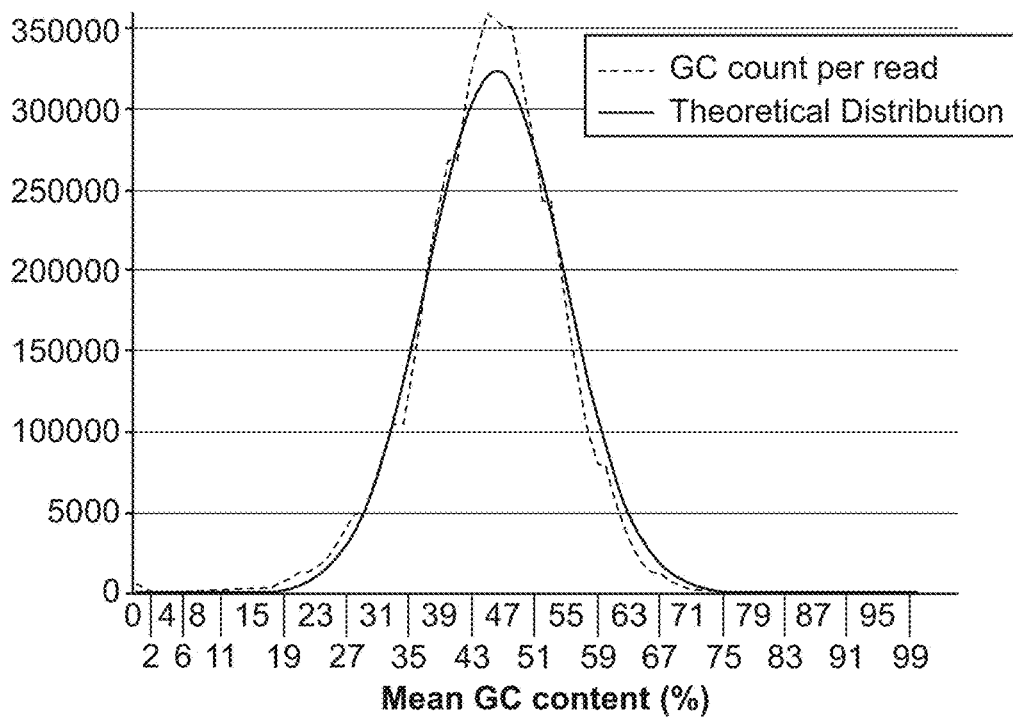

FIGS. 11A-11F show FastQC analytics on filtered read information for additional strand specific library methods, Shotgun (SHO) (FIGS. 11A, 11C and 11E) and deoxy-Uracil marked (dU) (FIGS. 11B, 11D and 11F). Quality scores (FIGS. 11A and 11B), Base composition (FIGS. 11C and 11D), Percentage GC content (FIGS. 11E and 11F).

Figure 12:
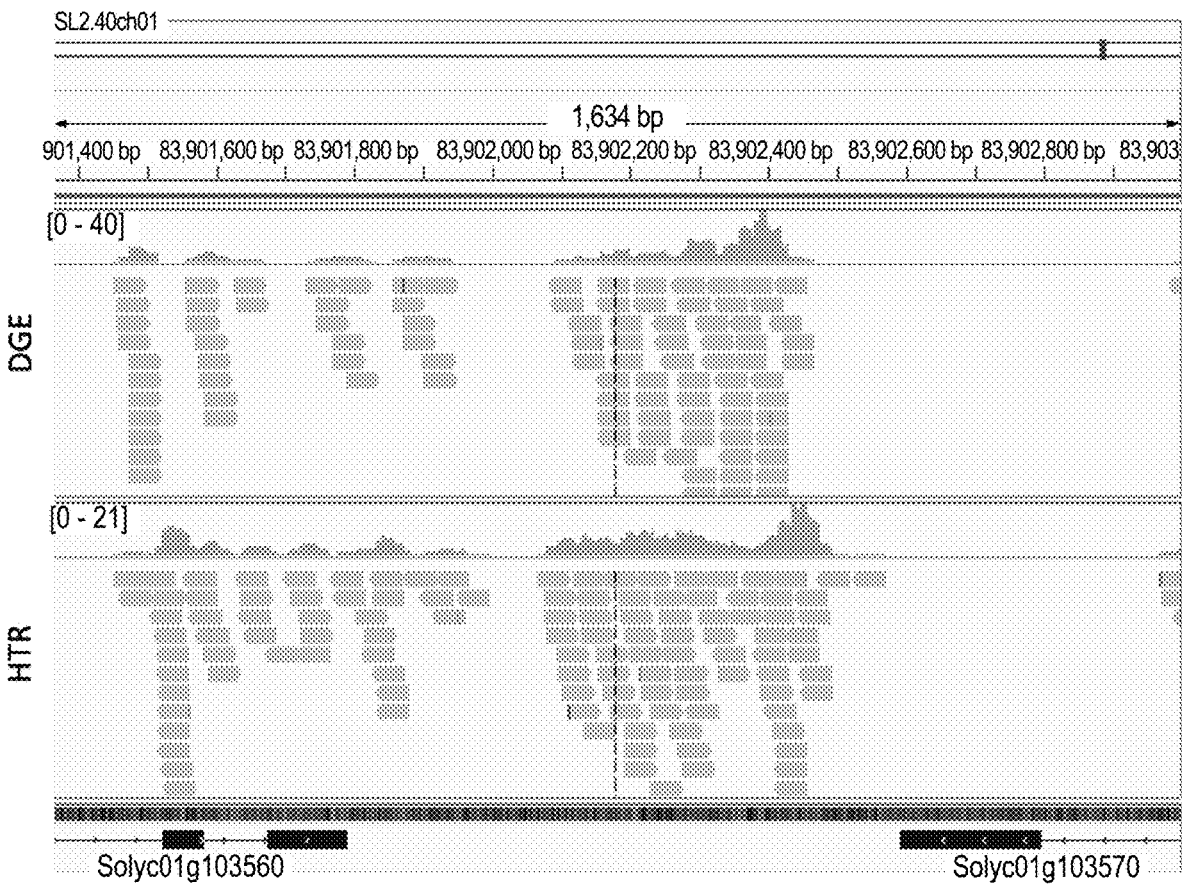

FIG. 12 provides the genomic mapping location of uniquely mapped reads in DGE and HTR. DGE reads show predominant localization to 3-prime of transcripts.

Figure 13:
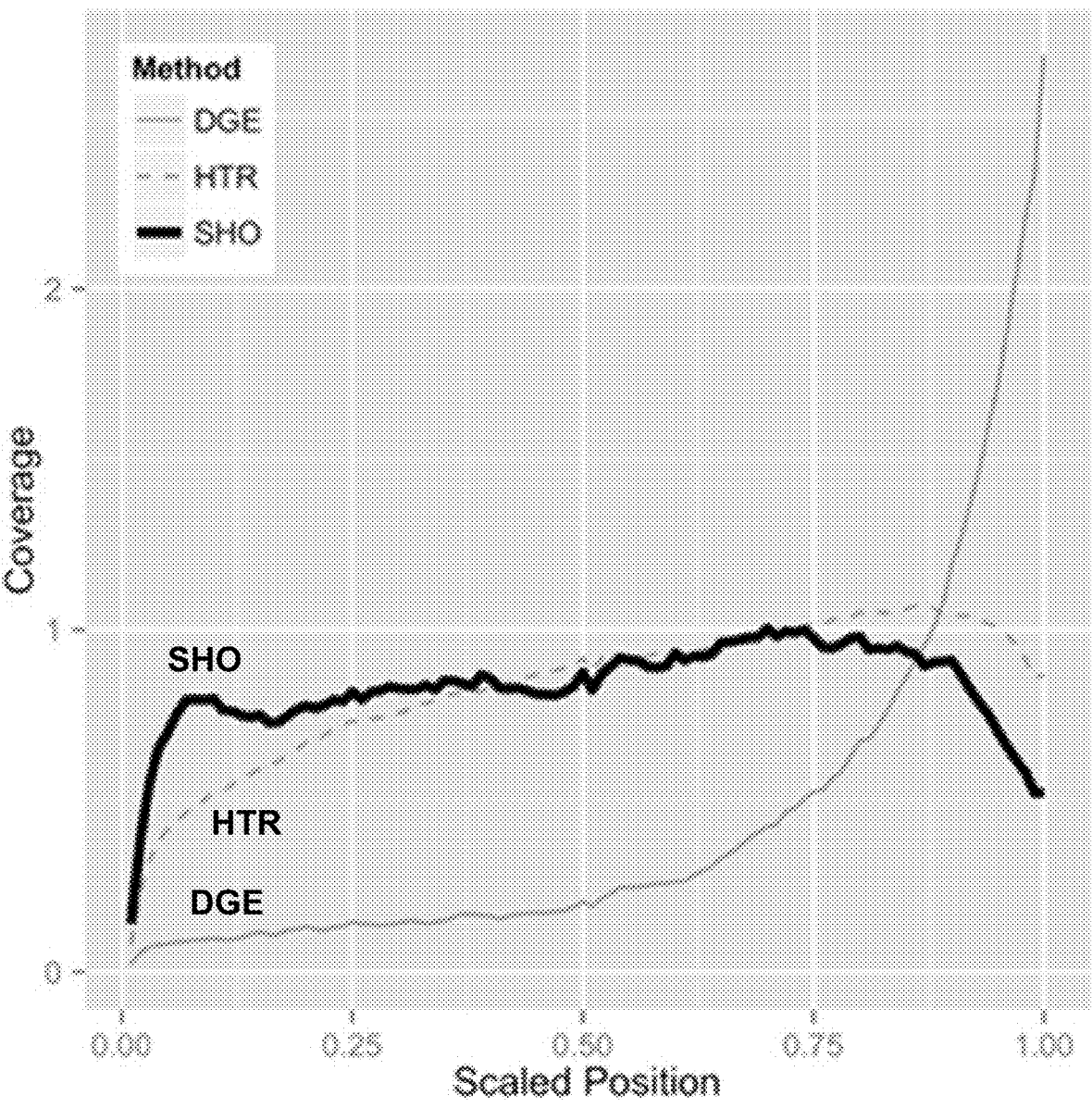

FIG. 13 shows a transcript coverage trace for SHO libraries.

Figure 14:
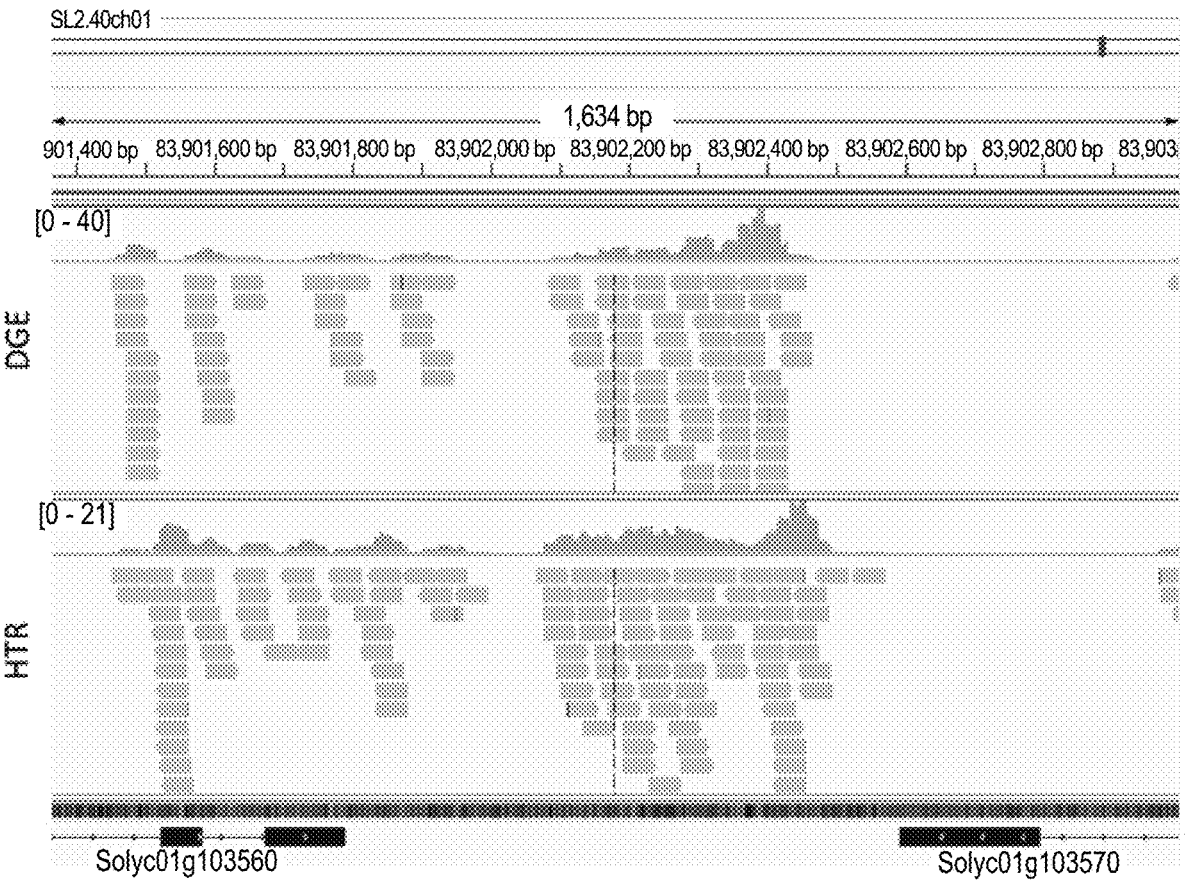
Figure 15A:
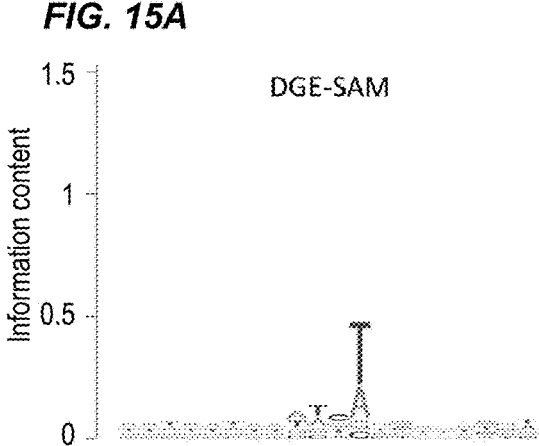
Figure 15B:
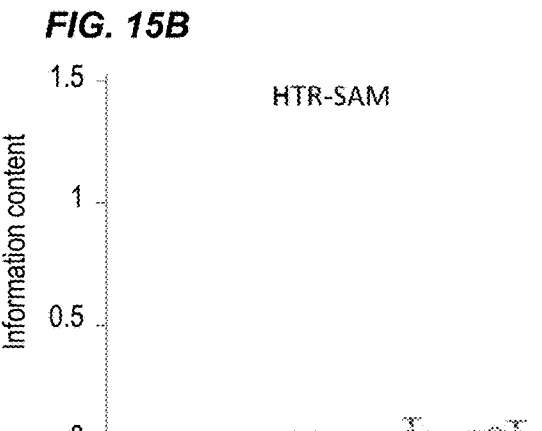
Figure 15C:
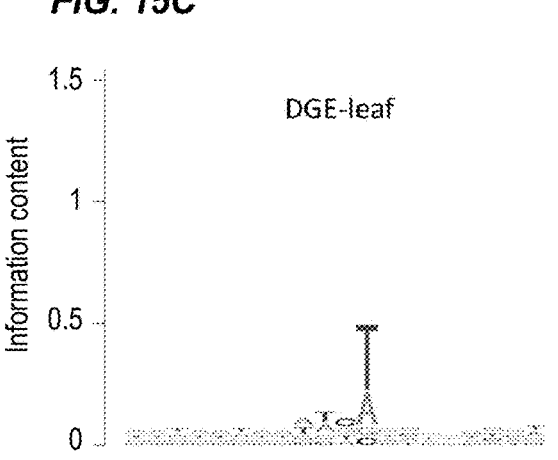
Figure 15D:
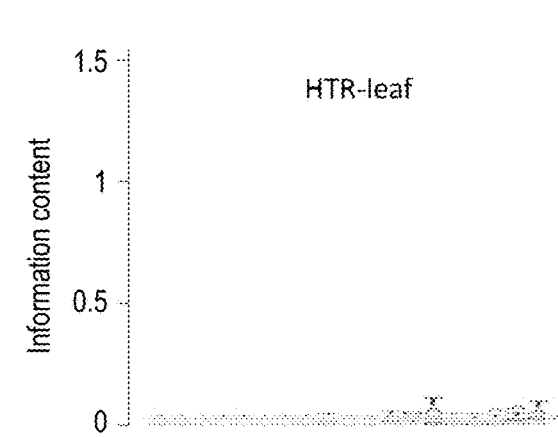

FIG. 14 shows the discrimination of read origin. DGE reads can be positively assigned to their transcript of origin when transcripts overlap or are in close proximity by strand specificity of the reads.

FIGS. 15A-15D show sequence logos displaying information content for 20 bases upstream of mapped reads.

Figure 16:
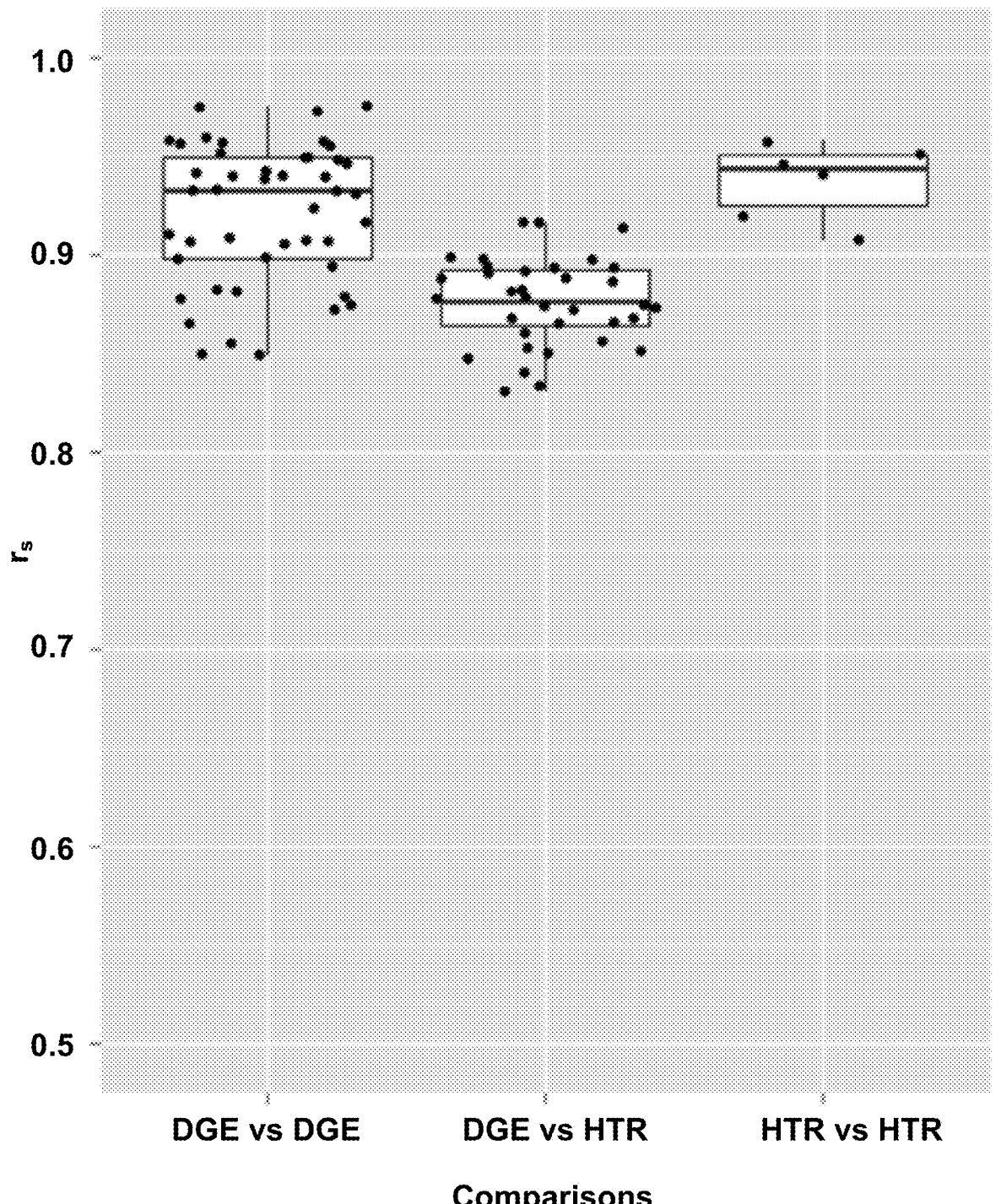

FIG. 16 provides pairwise comparisons of differential gene expression showing higher correlation within each method than between methods.

Figure 17:
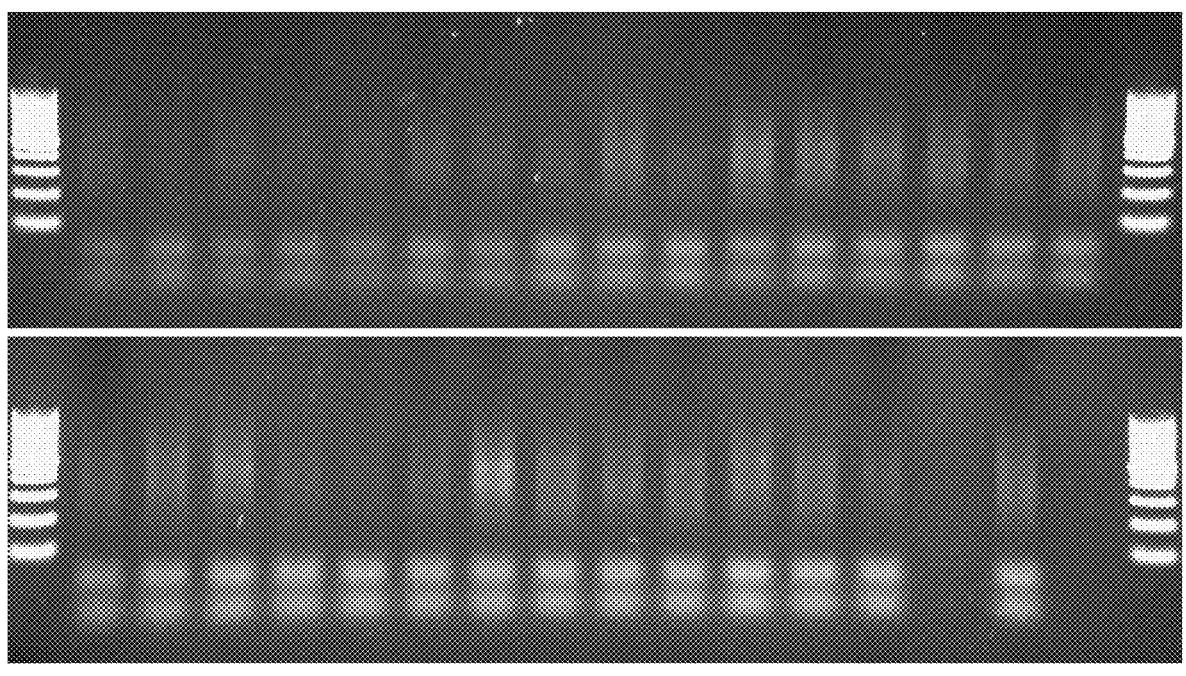

FIG. 17 shows heterogeneous amplification from identical mRNA samples by single-stranded adapters containing barcode sequences near the 3-prime end.

Figure 18:
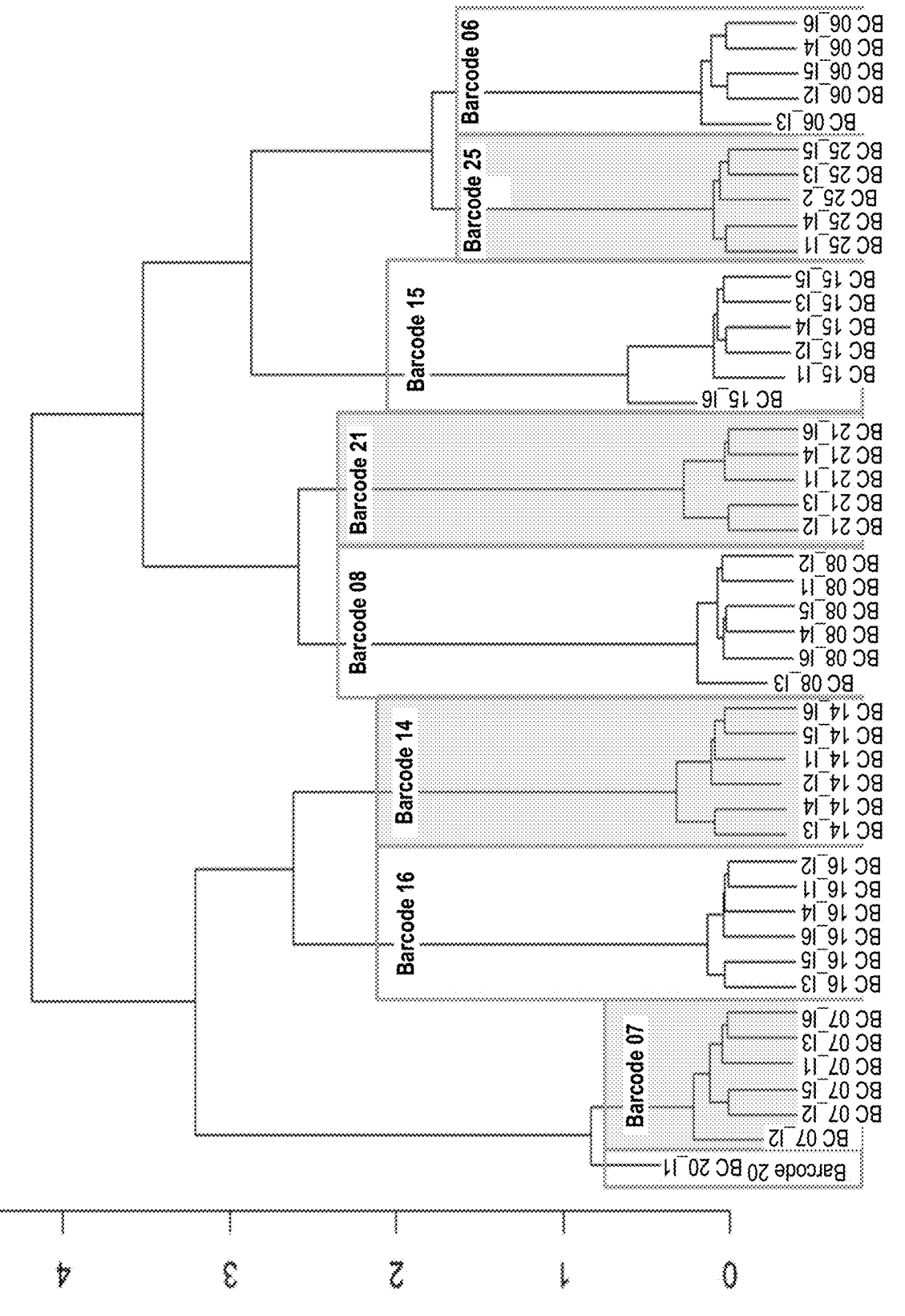

FIG. 18 depicts hierarchical clustering of library samples made with single stranded barcode containing adapters shows grouping only by barcode sequence.

Figure 19:
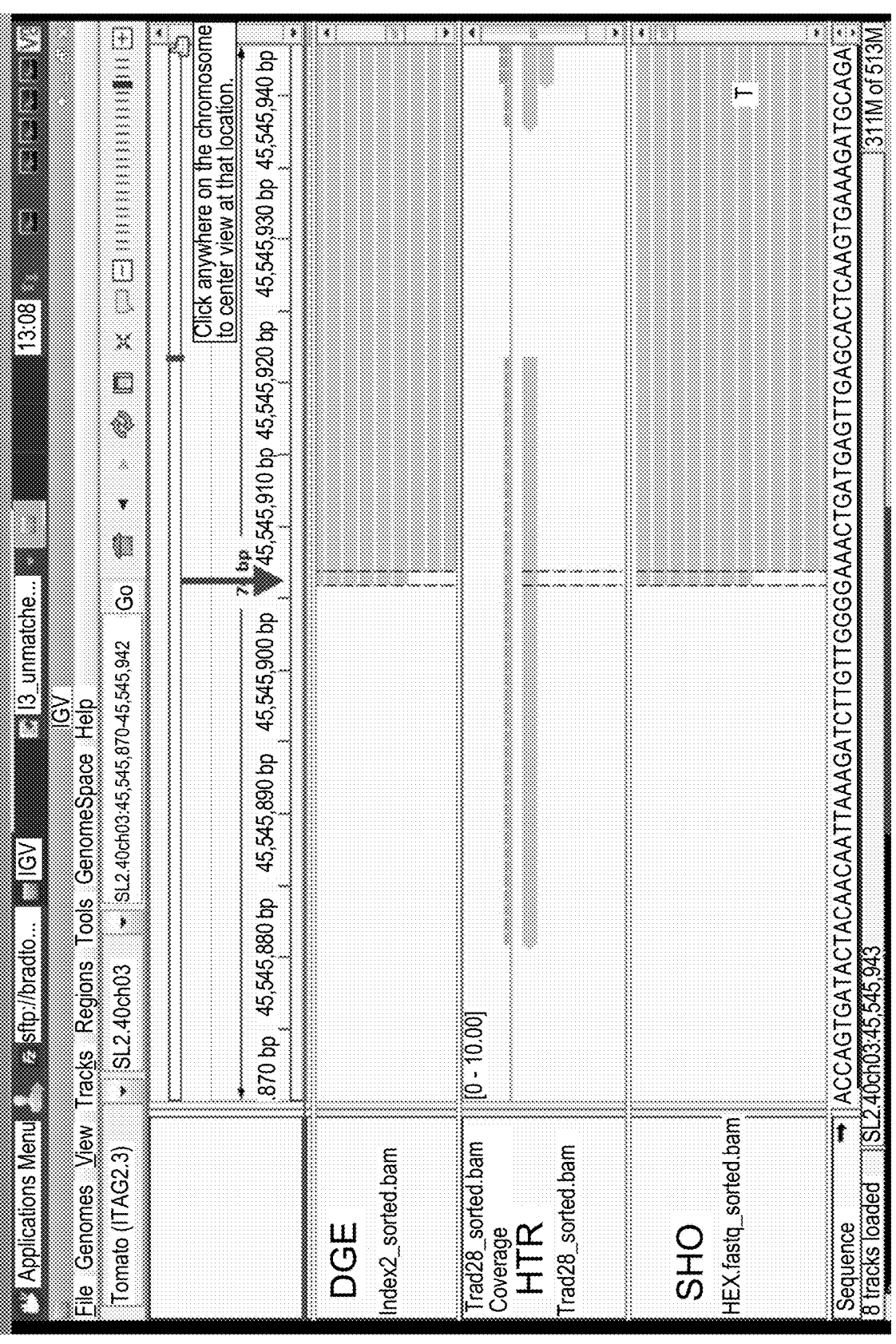

FIG. 19 shows overrepresentation of reads mapping to positions containing guanine repeats.

Figure 20:
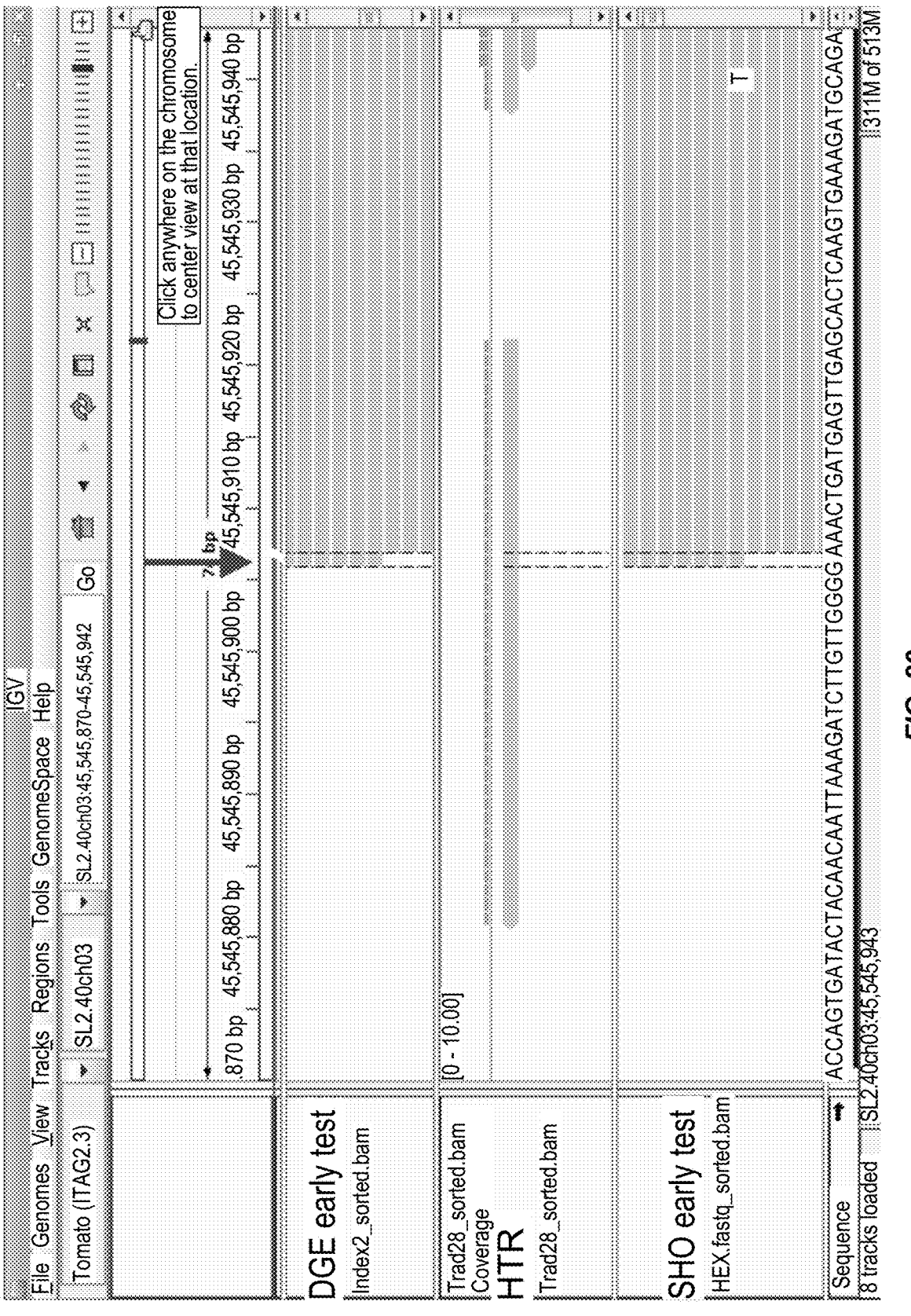

FIG. 20 shows highly uneven distribution of mapping locations in libraries made with prototype adapters.

Figure 21:
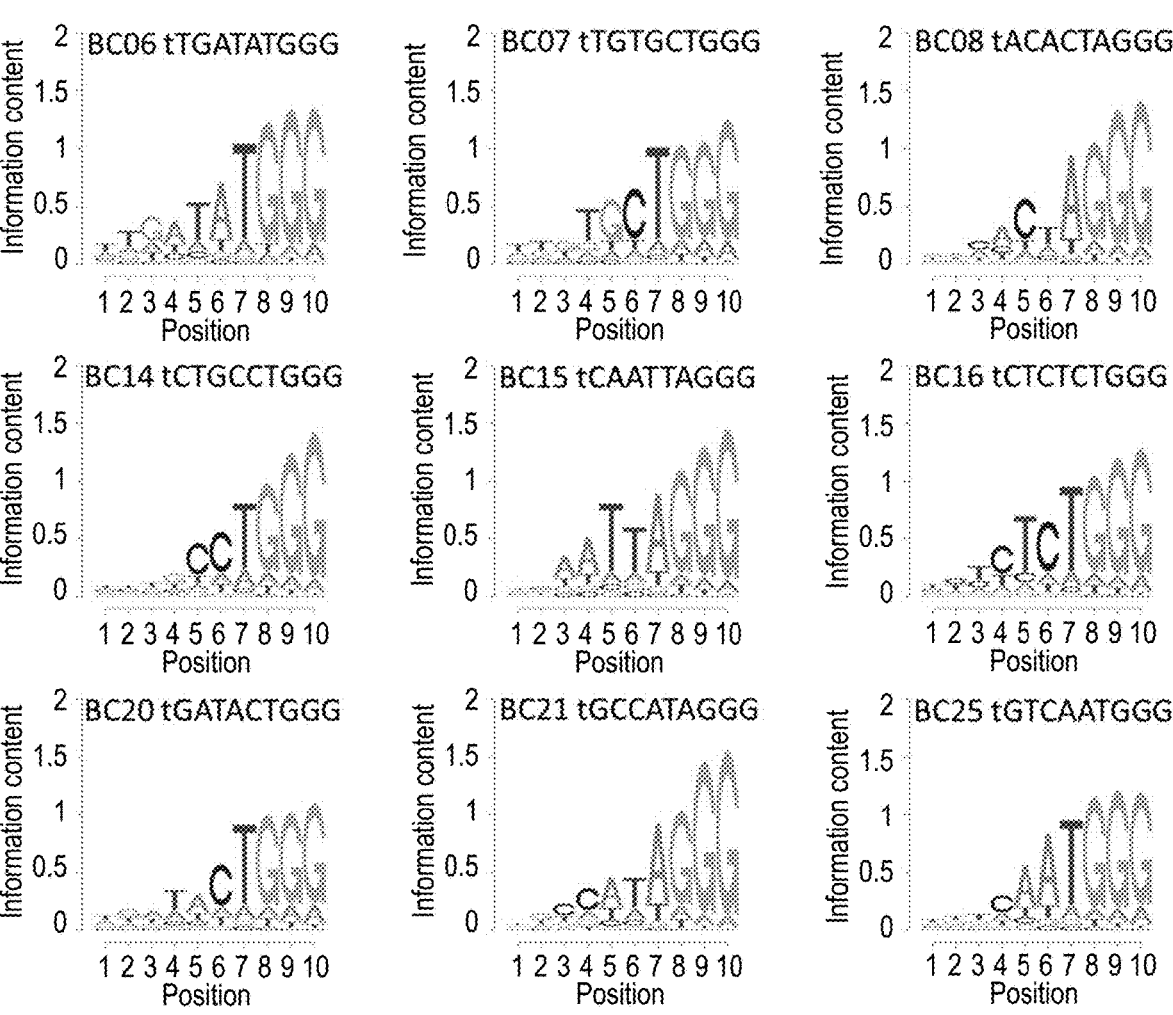

FIG. 21 shows sequence information content for reads upstream of the first mapping nucleotide for the trimmed reads. (BC06-BC08=SEQ ID NOS:22-24, BC14-BC16=SEQ ID NOS:25-27 and BC20-22=SEQ ID NOS: 28-30)

Figure 22:
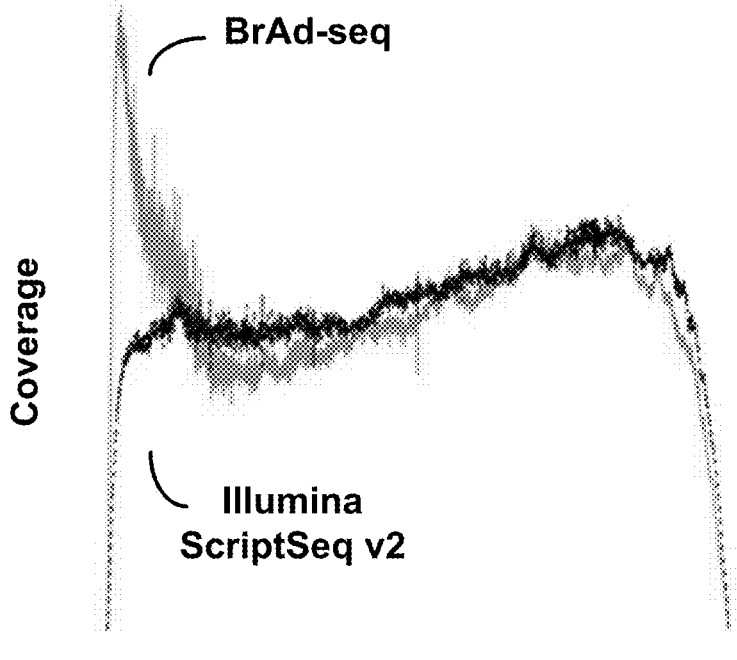

FIG. 22 provide read coverage by position in transcript using the method described herein (BrAD-seq) and Illumina ScriptSeq v2.

DETAILED DESCRIPTION OF THE INVENTION

I. Introduction

Provided herein are compositions, kits and methods for the production of strand specific RNA-seq libraries that can be used in Next Generation Sequencing (NGS). These less time-consuming and more cost-effective methods for generating strand-specific cDNA libraries exploit the phenomenon of DNA breathing to promote the capture and incorporation of directional sequencing adapters into double-stranded nucleic acid molecules. At a given temperature for a particular sequence, double-stranded nucleic acid molecule (e.g., a RNA-cDNA complex) may momentarily separate to expose the bases ("breathe"). This process happens at a higher rate at the terminal ends of a double stranded nucleic acid molecule. During the transient terminal breathing, a polynucleotide adapter can anneal to the first cDNA strand of the RNA-cDNA complex. In the presence of a polymerase, the adapter can extend and produce a second strand cDNA complementary to the first cDNA strand. The adapter incorporated double-stranded cDNA molecules are ready for amplification. This procedure avoids the requirement for second strand cDNA synthesis and removal of RNA prior to adapter addition. The methods described herein can be used to create strand specific RNA libraries and 3' Digital Gene Expression libraries.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "strand specific" or "directional" refers to the ability to differentiate in a double-stranded polynucleotide between the original template strand and the strand that is complementary to the original template strand.

The term "polynucleotide" or "nucleic acid" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides.

The term "RNA molecule" or "ribonucleic acid molecule" refers to a polynucleotide having a ribose sugar rather than deoxyribose sugar and typically uracil rather than thymine as one of the pyrimidine bases. An RNA molecule of the invention is generally single-stranded, but can also be double-stranded. In the context of an RNA molecule from an RNA sample, the RNA molecule can include the single-stranded molecules transcribed from DNA in the cell nucleus, mitochondrion or chloroplast, which have a linear sequence of nucleotide bases that is complementary to the DNA strand from which it is transcribed.

The term "cDNA molecule" or "complementary DNA molecule" refers to a synthetic DNA reverse transcribed from RNA through the action of a reverse transcriptase. The cDNA molecule may be double stranded, wherein one strand has a sequence that is substantially identical to a part of an RNA sequence and a second strand that is a complement thereof.

The term "first strand synthesis" can refer to the synthesis of the first strand using the original nucleic acid (e.g., RNA) as a starting template for the polymerase reaction. The nucleotide sequence of the first strand corresponds to a sequence that is complementary to the starting template. For example, in first strand synthesis using RNA as the starting template and reverse transcriptase (e.g., a RNA-dependent DNA polymerase), the resulting first strand (e.g., first strand cDNA) corresponds to the complementary sequence of the RNA template.

The term "first strand cDNA" refers a cDNA strand synthesized by first strand synthesis. The sequence of the first strand cDNA is complementary to the starting template of the first strand synthesis.

The term "second strand cDNA" refers a second strand of cDNA generated by an extension or polymerase reaction that uses a first strand cDNA from a first strand synthesis reaction as a template. The nucleotide sequence of the second stand cDNA corresponds to the sequence of the original nucleic acid template of the first strand synthesis (e.g., the RNA template).

The term "primer" or "oligonucleotide" refers to a short polynucleotide, generally with a free 3'—OH group, that bind to a target oligonucleotide, target polynucleotide, or template polynucleotide by hybridizing with the target or template.

The term "adapter" or "adapter molecule" refers an oligonucleotide of known sequence that can be annealed to a target polynucleotide or a target polynucleotide strand of interest and enables the generation of amplification products of the target polynucleotide or the target polynucleotide strand of interest. Suitable adapters include double-stranded nucleic acid (DNA or RNA) molecules comprising a single-stranded overhang of 1, 2, 3, 4, 5, 6, 7, 8, 9, 10, 11, 12, 13, 14, 15 bases or longer. The double-stranded DNA portion of the adapter can further comprise indexing or bar-coding sequences designed to mark either the samples or sequences of interest.

The term "extension," "extending" or grammatical equivalent thereof, refers to the addition of dNTPs to a primer, polynucleotide or other nucleic acid molecule by an extension enzyme such as a polymerase.

The term "ligation," "ligating" or grammatical equivalent thereof, refers to the joining of two nucleotide strands by a phosphodiester bond. Such a reaction can be catalyzed by a ligase. A ligase refers to a class of enzymes that catalyzes this reaction with the hydrolysis of ATP or a similar triphosphate.

The term "hybridization," "hybridizing" or grammatical equivalent thereof, refers to a reaction in which one or more polynucleotides react to form a complex that is formed at least in part (typically stabilized) via hydrogen bonding between the bases of the nucleotide residues. The hydrogen bonding can occur by Watson-Crick base pairing, Hoogstein binding, or in any other sequence-specific manner.

The term "reverse transcription" refers to the process of copying the nucleotide sequence of a RNA molecule into a DNA molecule. Reverse transcription can be done by reacting an RNA template with a RNA-dependent DNA polymerase (also known as a reverse transcriptase) under well-known conditions. A reverse transcriptase is a DNA polymerase that transcribes single-stranded RNA into single stranded DNA. Depending on the polymerase used, the reverse transcriptase can also have RNase H activity for subsequent degradation of the RNA template.

The term "random," in the context of a nucleotide sequence, refers to a varied sequence of nucleotides that when combined with other random nucleotide sequences in a population of polynucleotides represent all or substantially all possible combinations of nucleotides for a given length of nucleotides. For example, because of the four possible nucleotides present at any given position, a sequence of two random nucleotides in length has 16 possible combinations, a sequence of three random nucleotides in length has 64 possible combinations, or a sequence of four random nucleotides in length has 265 possible combinations.

The term "complementary," in the context of two nucleic acid sequences, refers to the ability to hybridize or base pair between nucleic acids, such as, for instance, between a first polynucleotide and a second polynucleotide. Complementary nucleotides are, generally, A and T (or A and U), or C and G. Two single-stranded polynucleotides are said to be substantially complementary when the bases of one strand, optimally aligned and pair with at least about 80% of the bases of the other strand, usually at least about 90% to 95%, and more preferably from about 98 to 100%.

III. Detailed Description of the Embodiments

Provided herein are methods, compositions and kits for constructing a strand-specific cDNA library that preserves directional information of the original single-stranded nucleic acid molecule. The present invention is based, in part, on the discovery of novel adapters that can specifically anneal to the 3' end of cDNA in a cDNA-RNA duplex and extend to generate a strand-specific cDNA molecule.

Under certain conditions, the 5' double-stranded DNA adapter (capturing-blocking adapter) can be annealed to a cDNA-RNA duplex undergoing breathing. Upon formation of an intermediate complex comprising the cDNA-RNA duplex and the DNA adapter, nucleotides can be added to the 3' terminus of the capturing strand of the adapter via extension by a DNA polymerase. The added nucleotides (e.g., the second strand cDNA or target polynucleotides) are complementary and possess directionality with respect to the cDNA strand of the cDNA-RNA duplex. The methods described herein are useful for creating strand-specific 3' Digital Gene Expression (3' DGE) libraries which provide readouts from the 3' end of the target mRNA. The methods and compositions can be combined with well-known sequencing techniques, especially high-throughput sequencing techniques, discovery applications include identifying alternative splicing events, gene fusions, allele-specific expression, and examining rare and novel transcripts.

A. Adapters

The adapters provided herein include a capturing primer and a blocking primer wherein the blocking primer is complementary to a portion of the capture primer. One of skill will recognize that the blocking primer need not be 100% complementary the capture primer and may be substantially complementary (e.g., 80%, 85%, 86%, 87%, 88%, 89%, 90%, 91%, 92%, 93%, 94%, 95%, 96%, 97%, 98% or 99% complementary). The nucleic acid sequences of the adapter may be based on the downstream application of the strand specific cDNA molecule of the present invention. For instance, the adapter sequence can be selected to be compatible with a specific NGS platform.

In some embodiments, the capturing primer of the adapter includes at least 20 deoxyribonucleotides that are complementary to the blocking primer. The capturing primer also includes a capturing region of about 6 to about 12, e.g., about 6, about 7, about 8, about 9, about 10, about 11, about 12, deoxyribonucleotides at the 3' end that can anneal to the 3' end of the target first strand cDNA. The 3' overhang of the double-stranded adapter molecule is formed by the about 6 to about 12, e.g., about 6, about 7, about 8, about 9, about 10, about 11, about 12, deoxyribonucleotides of the capture region located at the 3' end of the capture primer. The sequence of the deoxyribonucleotides of the capture region (i.e., 3' overhang) may be random. In other words, these deoxyribonucleotides may be selected randomly without consideration or knowledge of the sequence of the first strand cDNAs. In other cases, the sequence of the capture region may be a substantially random sequence, consensus sequence or specific sequence. In some embodiments, the deoxyribonucleotides of the 3' overhang are substantially complementary, e.g., 80%, 85%, 86%, 87%, 88%, 89%, 90%, 91%, 92%, 93%, 94%, 95%, 96%, 97%, 98% or 99% complementary, to one or more preselected first strand cDNAs. In other embodiments, the deoxyribonucleotides of the 3' overhang are selected to be 100% complementary to one or more preselected first strand cDNAs.

In some embodiments, the blocking primer of the double-stranded adapter molecule includes at least 20, e.g., 20, 25, 30, 35, 40, 45, 50, or more, deoxyribonucleotides that are complementary to a portion of the capturing primer that does not form the 3' overhang of the adapter molecule. The blocking primer may be the reverse complement of a portion of the capturing primer. The 5' end of the blocking primer can be phosphorylated.

In some cases, the capturing primer comprises the nucleic acid sequence of SEQ ID NO:1 (5'-CCTA-CACGACGCTCTTCCGATCT). The capturing primer with a capturing region may have the nucleic acid sequence of SEQ ID NO:3 (5'-CCTACACGACGCTCTTCCGATCTN6-12, wherein N can be any deoxyribonucleotide). In some embodiments, the capturing primer with a capturing region has the nucleic acid sequence of SEQ ID NO:4 (5'-CCTA-CACGACGCTCTTCCGATCTNNNNNN), SEQ ID NO:5

(5'-CCTACACGACGCTCTTCCGATC NNNNNNN), SEQ
ID NO:6 (5'-CCTACACGACGCTCTTCC-
GATCTNNNNNNNNN), SEQ ID NO:7 (5'-CCTA-
CACGACGCTCTTCCGATC NNNNNNNNN), SEQ ID
NO:8 (5'-CCTACACGACGCTCTTCCGATC
NNNNNNNNNN), SEQ ID NO:9 (5'-CCTA-
CACGACGCTCTTCCGATCTNNNNNNNNNNNN), or
SEQ ID NO:10 (5'-CCTACACGACGCTCTTCC-
GATCTNNNNNNNNNNNNNN). In some cases, the blocking
primer comprises the nucleic acid sequence of SEQ ID NO:2
(5'-AGATCGGAAGAGCGTCGTGTAGG).

It is contemplated that the partially double-stranded 5'
adapter can be based on any 5' adapter used for a number
NGS sequencing platforms, including for example, those
commercialized by Illumina®, Roche Diagnostics®,
Applied Biosystems®, Pacific Biosciences®, Thermo Fisher
Scientific®, Bio-Rad®, and the like. The sequence of the
capturing primer and its corresponding blocking primer can
be selected based on a specific adapter and the sequence of
the capturing region of the capturing primer can be random
or based on sequences of the first strand cDNAs of interest
or RNA molecules of interest.

The double-stranded 5' adapter can be produced by
annealing the capturing primer and the blocking primer
under conditions wherein a complex is formed having a 3'
overhang. In some instances, the 3' overhang is about 6 to
about 12, e.g., about 6, about 7, about 8 about 9, about 10,
about 11, about 12, random consecutive deoxyribonucle-
otides in length. The primers can be annealed under the
following conditions: (1) 94° C. for 1 minute, (2) 94° C. for
10 sec for 60 cycles with −1° C./cycle, (3) 20° C. for 1
minute, and optionally, 4° C. hold. In some cases, the
resulting double-stranded 5' adapter is separated from any
unannealed, free capturing primer and blocking primer.

To generate a strand-specific cDNA library comprising a
plurality of cDNA molecules (e.g., first and second strand
cDNAs), a plurality of partially double-stranded adapter
molecules can be used. In some embodiments, the sequences
of the capturing primer and blocking primer for each adapter
molecule are the substantially the same and the sequences of
the 3' overhangs of the adapter molecule may be random.

B. Methods of Generating a Strand-Specific cDNA Library

The methods described herein include producing a strand
specific cDNA library from a mixture of RNA-cDNA
duplexes derived from a biological sample. Detailed
descriptions of generating such as mixture of RNA-cDNA
duplexes are found in, e.g., Kumar et al., *Front Plant Sci,*
2012, 3:202; "mRNA Sequencing: Sample Preparation
Guide", Illumina, Cat. #RS-930-1001, Part #1004898;
Maekawa et al., Methods Mol Biol, 2014, 1164:51-65, and
Tariq et al., Nucl Acids Res, 2011, 39(18):e120.

The sample can be any biological sample, such as a
sample from an animal, plant, mold, fungi, or microorgan-
ism, e.g., bacteria, yeasts, viruses, viroids. RNA (e.g.,
mRNA and non-mRNA) from the biological sample can be
obtained or purified using standard techniques known in the
art. Kits and reagents, such as PureLink® RNA Mini kit
(Thermo Fisher Scientific), Dynabeads® mRNA DIRECT™
Micro Purification Kit (Thermo Fisher Scientific), GeneJET
RNA Purification Kit (Thermo Fisher Scientific), TRIzol®
(Thermo Fisher Scientific), and RNeasy® Plus Universal
Kits (Qiagen), may be used to lyse a biological sample and
extracting an RNA sample. A directional cDNA library can
be produced according to the methods described herein from
a small amount of biological sample, such as 10 mg of
cytoplasmically dense plant tissue or an equivalent thereof.

The RNA sample may be further processed to isolate
RNA molecules, e.g., mRNA and microRNA. Kits, such as
Dynabeads® mRNA Purification Kit, mRNA Isolation Kit
(Roche) and Isolation of mRNA Kit (New England Biolabs)
can be used. Alternatively, the RNA sample may be depleted
of ribosomal RNA (rRNA) using any method known to
those skilled in the art. Ribosomal RNA depletion kits are
commercially available from Qiagen, Thermo Fisher Scien-
tific, New England Biolabs, Illumina, and the like.

Prior to reverse transcription to generate RNA-cDNA
duplexes, the isolated RNA molecules (e.g., mRNA mol-
ecules) can be fragmented by partial alkaline hydrolysis
using divalent cations (e.g., $Zn^{2+}$ and $Mg^{2+}$) under an
elevated temperature (e.g., 90° C.-96° C.). Fragmentation
buffers are commercially available from, for example, New
England Biolabs® and Thermo Fisher Scientific®. Alterna-
tively, a first strand cDNA synthesis buffer containing $Mg^{2+}$
ions may be used to fragment mRNA at a high temperature.
In some embodiments, the isolated RNA molecules are not
fragmented. The unfragmented RNA molecules can be used
to make full-length transcript libraries.

The fragmented or unfragmented mRNA molecules can
be primed with a 3' adapter that is compatible with a
downstream application, e.g., a specific NGS platform. For
instance, a polyT primer or a random primer (e.g., random
hexamer or octamer) fused to a 3' adapter can be annealed
to the mRNA molecules.

The RNA-cDNA duplexes can be produced from the 3'
adapter primed RNA molecules described above by standard
first strand cDNA synthesis reaction methods. For instance,
a first strand cDNA reaction mixture comprising a reverse
transcription buffer, DTT, dNTPs and reverse transcriptase
can be admixed with the 3' adapter primed RNA molecules
under conditions to synthesize first strand cDNA.

The double-stranded 5' adapter described above can be
added to an RNA-cDNA duplex under conditions to form an
intermediate complex comprising the RNA molecule, the
first cDNA strand, and the adapter. In some embodiments,
the intermediate complex is formed at 20° C. to 25° C. in the
presence of cation ions (e.g., $Mg^2$). The multimeric, inter-
mediate complex can be produced when the RNA-cDNA
duplex transiently opens at a terminal end allowing the 5'
adapter's capturing single-stranded extension (e.g., 3' over-
hang) to anneal to the 3' end of the cDNA strand. The
complex may be further stabilized by extension of the
capturing primer of the adapter.

In some aspects, the method includes extending the 5'
adapter, e.g., the capturing primer that is hybridized to the
first strand cDNA. In some cases, synthesizing the second
strand cDNA from the first strand cDNA includes extending
the hybridized capturing primer. Methods for a primer
extension are well known to one of ordinary skill in the art
and may include using extension enzymes, such as poly-
merases. Useful DNA polymerases include a polymerase
with 5' to 3' exonuclease activity; a polymerase with strand
displacement activity; DNA polymerase I (Pol I); DNA
polymerase I, Large (Klenow) Fragment, and Klenow Frag-
ment exo-. In some cases, the DNA polymerase with strand
displacement activity can be phi 29, Bst DNA Polymerase,
Large Fragment; SD DNA polymerase, a modified DNA
polymerase derived from *Thermus aquaticus* (Taq poly-
merase) and the like. The second strand cDNA of the present
invention is produced by primer extension and includes the
capturing primer. In some embodiments, a strand specific
cDNA is generated from the 3' end of the cDNA priming on
the capturing primer.

C. Amplification of Strand-Specific cDNAs

Any method, composition and kit can be used to generate amplification-ready products of the strand-specific cDNAs for downstream applications such as massively parallel sequencing (i.e., next generation sequencing methods) or hybridization platforms. In some instances, enrichment PCR is performed using primers that are compatible with the 5' and 3' adapters of the cDNA molecules and can amplify the adapters and the cDNA molecules. Methods of amplification are well known in the art. Suitable amplification reactions can include any DNA amplification reaction, including but not limited to polymerase chain reaction (PCR), strand displacement amplification (SDA), linear amplification, multiple displacement amplification (MDA), rolling circle amplification (RCA), single primer isothermal amplification (SPIA), Ribo-SPIA, or a combination thereof.

In PCR, the two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. The reiterative cycling of denaturation, primer annealing, and primer extension by the polymerase results in the exponential increase in copies of the desired sequence of the target polynucleotide flanked by the primers.

D. Next Generation Sequencing

In some embodiments, the method provided herein includes DNA sequencing an amplification product whose sequence corresponds to the target RNA molecule. Non-limiting examples of DNA sequencing include automated Sanger sequencing (AB 13730×1 genome analyzer), pyro-sequencing on a solid support (454 sequencing, Roche), sequencing-by-synthesis with reversible terminations (Illumina® Genome Analyzer), sequencing-by-synthesis using semiconductors (Ion Torrent™), sequencing-by-ligation (ABI SOLiD®) or sequencing-by-synthesis with virtual terminators (HeliScope™). Useful methods for sequencing have been commercialized by Illumina, 454/Roche Life Sciences, Applied Biosystems, Helicos Biosciences, Pacific Biosciences, Life Technologies, and the like.

E. Kits

Provided herein is a kit including a partially double-stranded 5' adapter and a sequencing primer useful for sequencing the 5' adapter. The 5' adapter can include a capturing primer comprising at least 20 deoxyribonucleotides and a 3' overhang comprising about 6-12 consecutive deoxyribonucleotides, and a blocking primer comprising at least 20 deoxyribonucleotides complementary to at least a portion of the capturing primer. The blocking primer may be 100% complementary to the capturing primer over the length of the blocking primer. The 6-12 consecutive deoxyribonucleotides that form the 3' overhang may be random or represent a preselected sequence based on the first strand cDNAs of interest. In some instances, the preselected sequence is at least 50%, e.g., 50%, 55%, 60%, 65%, 70%, 75%, 80%, 85%, 90%, 95% or 99%, complementary to a terminal end of the cDNA of interest. In other instances, the preselected sequence is 100% complementary to a terminal end of the cDNA of interest.

The sequencing primer of the kit is used to determine the sequence the second strand cDNA generated according to the methods described herein. The sequence of the sequence primer is based on the 5' adapter molecule. In some embodiments, the sequencing primer is complementary to the blocking primer of the adapter.

The kit can include reagents needed to perform generate a strand-specific cDNA library, such as, polymerase buffers, polymerases, DTT, dNTPs, sterile water, $MgCl_2$, fragmentation buffers, cDNA amplification primers, and reagents for purifying the library. The kit can also contain an instruction manual.

IV. Examples

The following examples are offered to illustrate, but not to limit the claimed invention.

Example 1: Breath Adapter Directional Sequencing (BrAD-Seq): A Streamlined, Ultra-Simple and Fast Library Preparation Protocol for DNA and Strand-Specific mRNA Library Construction Next Generation Sequencing (NGS) technologies have rapidly become foundational tools of genomics research (Koboldt et al., 2013). In particular, RNA-sequencing (RNA-seq) has transformed gene expression analyses and promoted the study of non-model organisms at an unprecedented level of detail with the ability to generate transcriptome assemblies for virtually any species (Sémon, 2014). On the most commonly used Illumina platform the ability to sequence a large number of biological samples requires the creation of libraries from nucleic acid samples with specified sequence "adapters" at the termini of the molecules. There are a variety of methods available to generate adapter-added libraries from nucleic acid samples from a variety of source materials, however the process still remains technically challenging, laborious, and expensive, thereby limiting widespread access to the technology.

Here we present a novel and efficient method for constructing strand specific RNA-seq libraries in a simple, rapid, and inexpensive modular format. The method is optimized to create strand specific 3-prime Digital Gene Expression (DGE—providing readout from the 3' end of the mRNA) and can be adapted for strand-specific non-DGE shotgun type (SHO) and more conventional non-strand specific (CNV) RNA-seq libraries, in addition to utilizing a variety of DNA source materials. 3-prime DGE libraries are often preferred for gene expression studies because a single mRNA yields approximately 1 sequence read reducing potential sources of bias.

Strand specific RNA-seq requires the directional addition of unique 5-prime and 3-prime adapter sequences during preparation of the cDNA libraries. This is accomplished in a number of ways among the various NGS library preparation protocols. These include, the ligation of a known sequence to the 5-prime portion of mRNA molecules prior to cDNA synthesis (Lister et al., 2008), removal of the template RNA strand followed by randomly primed 2nd strand synthesis (Armour et al., 2009), labeling of first or second strand cDNA molecules with dUTP for enzymatic degradation prior to enrichment (Parkhomchuk et al., 2009) and the use of terminal transferases to add defined nucleotides to the cDNA molecules (Zhu et al., 2001; Tang et al., 2010), with each method having advantages and shortcomings (Regev et al., 2012). Our method for directional NGS library construction considerably simplifies and accelerates the library construction process. Only around 10 milligrams of cytoplasmically dense plant tissue such as Shoot Apical Meristem (SAM) or leaf primordia (slightly larger amounts for mature tissue), are required for RNA-seq library production, and an individual worker can readily complete the procedure starting from tissue in a single day.

We utilize an aspect of nucleic acid chemistry that has not been exploited in available methods to generate strand specific libraries. Double stranded nucleic acids undergo a phenomenon called "breathing" where the individual strands will momentarily separate to expose the bases (von Hippel et al., 2013). This process happens at a higher rate at the ends of double stranded nucleic acids (von Hippel et al., 2013). We exploit this transient terminal breathing to incorporate an adapter oligonucleotide that includes the Illumina TruSeq PE1 sequence specifically at the 5-prime terminus of the RNA-cDNA duplex. Breath capture allows for streamlined strand-specific library protocols not requiring prior second strand synthesis or removal of template RNA, allowing construction of either 3-prime DGE or shotgun (SHO) type strand specific libraries.

From these basic strand specific modules we further developed additional compatible modules to accommodate a variety of nucleic acid species as input materials—single-stranded RNA, double-stranded DNA and single-stranded DNA. This provides a general purpose platform for creation of libraries for gene expression studies, genomic DNA libraries as well as from the products of amplification of minute samples such as DNA obtained in Chromatin Immunoprecipitation (ChIP) experiments and RNA from Laser Capture Microdissected (LCM) tissue samples. The use of common modules in this platform minimizes the number of individual reagents required to generate any number of library types, as well as standardizes the handling and manipulation steps, reducing the learning curve and minimizing the potential for human error.

Materials and Methods

A schematic diagram of the reaction steps for strand-specific library synthesis is shown in FIG. 1. Brief protocol for non-strand specific "conventional" (CNV) RNA-seq libraries can be found below. Detailed directions for strand specific DGE RNA-seq as well as strand specific SHO RNA-seq and non-strand CNV RNA-seq and DNA-seq protocol variants can also be found below. All oligonucleotides used in this study were ordered from Life Technologies (Thermo Fisher Scientific) at 50 nanomole scale, desalted with no additional purification.

A. Plant Material

Tomato seeds (*S. lycopersicum* cv M82: LA3475) were provided by the Tomato Genetics Resource Center, University of California, Davis. After sterilization (50% bleach for one minute followed by rinse with water), seeds were placed onto water-soaked paper towels in Phytatrays (Sigma) in the dark for three days at room temperature to allow germination. The germinated seeds within Phytatrays were placed into a growth chamber at 22° C. with 70% relative humidity and a photoperiod of 16 h light/8 h dark for another four days. Seedlings were then transplanted into Sunshine Mix soil (Sun Gro). After growing in soil for 11 days, P5 leaf primordia (the leaf sample) and SAM (consisting of the SAM and 4 younger leaf primordia) were dissected carefully using razor blades and harvested into RNase-free tubes.

B. mRNA Isolation

Tissues were processed and lysed as described previously by Kumar et al. (Kumar et al., 2012) using zircon beads and Lysate Binding Buffer containing Sodium dodecyl sulfate in place of Lithium dodecyl sulfate. mRNA was isolated from 200 µl of lysate per sample. 1 µl of 12.5 µM of 5-prime biotinylated polyT oligonucleotide containing a 5-prime nucleotide arbitrary spacer sequence followed by 20 thiamine nucleotides (5'-bio-ACAGGACAT- TCGTCGCTTCCTTTTTTTTTTTTTTTTTTTTT-3'; SEQ ID NO:11) was added to each lysate sample, mixed by pipetting several times and allowed to stand for 10 minutes. Following incubation, captured mRNAs were isolated from the lysate by the addition of 20 µl of LBB washed Streptavidin-coated magnetic beads (New England BioLabs, Cat. #S1420S). The bead-lysate mixture was mixed by pipetting and allowed to stand an additional 10 minutes. Samples were placed on a 96-well magnetic separator (Edge BioSystems, Cat. #57624) and washed as previously described (Kumar et al., 2012) with the following modifications. A) Wash volumes of WBA, WBB and LSB were 300 µl each and buffers were chilled on ice prior to use. B) mRNA elution was done into 16 µl of 10 mM Tris-HCl pH 8 containing 1 mM β-mercaptoethanol.

C. mRNA Fragmentation, 3-Prime Adapter Priming mRNA fragmentation was accomplished using magnesium ions at elevated temperature (FIGS. 7A-C). Priming for the cDNA synthesis reaction was carried out in a single reaction mixture for Strand Specific-DGE, Strand Specific-RND, and non-Strand Specific libraries were fragmented in a reaction containing 1.5 µl 5× RT buffer (Thermo scientific, Cat. #EP0441), 1 µl of priming adapter and 7.5 µl of the sample mRNA in a total reaction volume of 10 µl. Mixtures were spun down and incubated in a thermocycler. The following oligonucleotides and thermocycler programs were used for each library type.

DGE: 1 µl of 2 µM oligo L-3ILL-20TV.2 (5'-GTGACTG-GAGTTCAGACGTGTGCTCTTCC-GATCTTTTTTTTTTTTTTTTTTTTTTV-3'; SEQ ID NO:12) (25° C. for 1 second, 94° C. for 1.5 min, 30° C. for 1 min, 20° C. for 4 min, 20° C. at hold).

SHO: 1 µl of 5 µM oligo L-3ILL-N8.2 (5'-GTGACTG-GAGTTCAGACGTGTGCTCTTCC-GATCTNNNNNNNNN-3'; SEQ ID NO:13) (25° C. for 1 second, 94° C. for 1.5 min, 4° C. for 5 min, 20° C. at hold).

D. cDNA Synthesis cDNA was synthesized by addition of 5 µl of the following reaction mixture to the fragmented and primed mRNA: 1.5 µl 5× Thermo Scientific RT buffer (Thermo scientific, Cat. #EP0441), 1.5 µl 0.1M Dithiothreitol (DTT), 1 µl H2O, 0.5 µl 25 mM dNTPs (Thermo Scientific, Cat. #R1121), 0.5 µl RevertAid RT enzyme (Thermo Scientific, Cat. #EP0441) (total reaction volume 15 µl). The reaction mixture was set up at room temperature and placed in a thermocycler running the following program: (25° C. 10 min, 42° C. 50 min, 50° C. 10 min, 70° C. 10 min, 4° C. hold). cDNA was cleaned and size-selected prior to "breath capture" or second strand synthesis by addition of 5 µl 50 mM EDTA pH 8.0 and 30 µl Agencourt AMPure XP beads (Beckman, Cat. #A63881) to each sample and mixed by pipetting. After 5 minutes, samples were placed on a magnetic tray, supernatant was removed, and pellets were washed twice with 300 µl 80% ethanol without pellet disruption. Residual ethanol was removed with 20-µl pipette tip and samples were allowed to air-dry until no visible traces of liquid were detectable.

E. 5-Prime Duplex Breath Capture Adapter Addition (Strand Specific)

5-prime adapter addition was done by rehydrating the cDNA bound to bead-pellet with 4 µl 10 µM pre-annealed 5-prime double stranded adapter oligo at room temperature. Double stranded 5-prime adapter was prepared by making a stock solution containing 10 mM each of oligos 5pSense8n (5pSense8n 5'-CCTACACGACGCTCTTCC-GATCTNNNNNNNNN-3'; SEQ ID NO:4) and 5pAnti (5pAnti 5'-AGATCGGAAGAGCGTCGTGTAGG-3'; SEQ ID NO:2) in H₂O, dispensing to 100 μL volumes in strip tubes and annealing them in a thermocycler running the following program: [94° C. for 1 min (94° C. for 10 sec)×60 cycles–1° C./cycle, 20° C. for 1 min, 4° C. at hold]. Subsequently, 6 μl of the following reaction mixture was added, mixed by pipetting to fully re-suspend the pellet and incubated at room temperature for 15 minutes: 3.5 μl H₂O, 1 μl 10× Thermo Pol I reaction buffer (Thermo Scientific, Cat. #EP0041), 1 μl 250 mM MgCl₂ (made fresh and stored at –20° C.), 0.25 μl 25 mM dNTPs (Thermo Scientific, Cat. #R1121), 0.25 μl Thermo DNA Pol I (Thermo Scientific, Cat. #EP0041) (10 μl total reaction volume). The pre-enrichment libraries on beads were washed and size-selected using Agencourt AMPure XP beads present from the previous step by adding 10 μl 50 mM EDTA pH 8.0 and 30 μl ABR, mixed thoroughly by pipetting and allowed to stand for 5 minutes prior to placing on the magnetic tray. Supernatant was removed and pellets were washed twice with 300 μl 80% ethanol, without pellet disruption. Residual ethanol was removed with 20-μl pipette tip and samples were allowed to air-dry until no visible traces of liquid were detectable. Pellets were re-suspended in 22 μl 10 mM Tris pH 8.0, allowed to stand 1 minute and place on the magnetic tray. Supernatant was transferred without beads to fresh strip tubes and stored at –20° C. prior to enrichment.

F. PCR Enrichment and Index Sequence Addition (Strand-Specific and Non-Strand-Specific)

The enrichment step was done using full length oligonucleotides containing the full adapter sequence as well as short oligonucleotides complementary to the distal-most portion of the adapter arms to ensure predominantly full-length amplification products. PCR enrichment was carried out by combining 1 μl of the 2 μM uniquely-indexed ILL-INDEX oligonucleotide (ILL-INDEX 5'-CAAGCAGAAGACGGCAT-ACGAGATNNNNNNNNNGTGACTGGAGTTCA-GACGTGT GCTCTTCCGAT-3'; SEQ ID NO:14) with 9 μL of the master mix: 4 μl 5× Phusion HF Buffer, 2.6 μl H₂O, 1 μl 2 μM PE1 primer (PE1 5'-AATGATACGGCGAC-CACCGAGATCTACACTCTTTCCCTA-CACGACGCTCTTCCGA TCT-3'; SEQ ID NO:15), 1 μl 8 μM each S1+S2 primers (S1 5'-AATGATACGGCGAC-CACCGA-3'; SEQ ID NO:16, S2 5'-CAAGCAGAA-GACGGCATACGA-3'; SEQ ID NO:17), 0.2 μl 25 mM dNTPs, 0.2 μl Phusion Polymerase (Thermo Scientific, Cat. #F-530L) and 10 μl of pre-enrichment cDNA in a total reaction volume of 20 μl. Half of the PCR mix (10 μl) was placed in separate sample tubes stored at –20 C as backup for samples where more cycles of enrichment were needed. The remaining 10 μl were spun down and placed in a thermocycler using the program: [98° C. for 30 seconds, (98° C. for 10 seconds, 65° C. for 30 seconds, 72° C. for 30 seconds) for 11 cycles, 72° C. for 5 min, 10° C. for hold). Samples showing only very faint enrichment were re-amplified with 13 cycles of enrichment from the backup PCR samples. 2 μl of each library sample was run on a 1% agarose gel, with 1 μl of O'GeneRuler 100 bp DNA ladder (Thermo Scientific, Cat. #SM1143) for size and quantity reference, at 100 volts for 20 minutes. The remaining 8 μl of enriched library sample was cleaned and size selected using 12 μl of fresh Agencourt AMPure XP beads and washing twice with 80% ethanol as in previous wash steps. The libraries were eluted from the pellet with 10 μl 10 mM Tris pH 8.0, quantified, and pooled as previously described (Kumar et al., 2012). 50 bp single end sequencing was carried out at the Vincent J. Coates Genomic sequencing Facility at UC Berkeley.

G. Bioinformatics

Bioinformatics and statistical analysis was carried out using the iPlant Atmosphere cloud service (Goff et al., 2011). Reads were trimmed to 42 bp and quality filtered using FASTX-Toolkit (see, website at hannonlab.cshl.edu/fastx_toolkit/) and scripts developed by Comai lab, UC Davis (see, website at comailab.genomecenter.ucdavis.edu). Reads were mapped using Bowtie (Langmead et al., 2009) with the parameters specified in Table 1. Read quality analysis was performed using FASTQC (see, website at bioinformatics.bbsrc.ac.uk/projects/fastqc/). The code that was used to perform each of the bioinformatic steps is available at the website github.com/SinhaLab/townsley-fips-2015/and FASTQ files for RNA-seq data used in this study can be downloaded from Dryad data repository (link can only be provided in proof due to Dryad data hosting policies).

TABLE 1

| Differential gene expression calls for DGE and HTR library samples. | |
| --- | --- |
| fastx_trimmer | -f 9 -Q 33 |
| trimFastqQuality.py | 20 35 |
| read_N_remover.py | |
| adapterEffectRemover.py | 41 |
| Bowtie: | |
| non-strand specific, non-uniquely mapped | -a --best --strata -v 1 -p 4 --sam --tryhard |
| non-strand specific, uniquely mapped | -a --best --strata -m 1 -v 1 -p 4 --sam --tryhard |
| strand specific, uniquely mapped | -a --best --strata --norc -m 1 -v 1 -p 4 --sam --tryhard |

Results and Discussion

To evaluate our strand-specific library preparation method, we prepared Shoot Apical Meristem (SAM) and leaf primordium (Leaf) samples using the new BrAD-seq DGE method and our previously-developed HTR method for a pairwise comparative analysis. In this protocol we add sample-identifying index sequences to the library molecules during the enrichment stage (Meyer and Kircher, 2010).

A. Library Enrichment

Although as a matter of procedure we do not typically quantify mRNA concentration prior to library synthesis to maintain higher throughput, when beginning experiments with unfamiliar materials it can be of utility to have some idea how many enrichment cycles would be reasonable to try. To ascertain the relationship between the input mRNA concentration and the number of enrichment cycles chosen, 22 mRNA samples which were used for DGE library synthesis were quantified on a BIOANALYZER™ using the RNA 6000 Pico kit (Agilent Technologies). This information was correlated with the number of cycles used for enrichment of each library sample and the concentration of washed libraries (FIG. 8). The relationship suggests that below about 10 ng/μl of mRNA it may be worthwhile to start with about 14 enrichment cycles at the first attempt, although individual preferences in interpretation of gel images and targeted final concentrations for pooling of samples will ultimately be important factors in deciding on the ideal number of enrichment cycles.

B. Read Quality

To avoid inclusion of sequence originating from the 5-prime adapter capture strand, the first 8 bases of DGE libraries was trimmed prior to analysis. For HTR libraries the percentage of reads mapping was also found to be higher (77.8% vs. 74.1%) when the first 8 bases were trimmed, so for all analyses trimmed FASTQ files were generated for samples prior to the quality filtering step. The mapping rate improves in trimmed HTR libraries because during cDNA synthesis random primers anneal with mismatches, incorporating non-native sequence into cDNA molecules.

The overall quality scores for the raw DGE libraries was lower than HTR (FIG. 8) due to the inclusion of cDNA inserts containing polyA tracts. These low complexity sequences cannot be mapped to reference sequences and they are largely removed prior to mapping by quality filtering (FIG. 2A and FIGS. 9A-9B).

Since a population of strand-specific cDNA molecules highly enriched at the 3-prime of mRNA transcripts should be comprised of a smaller number of unique sequences for each transcript, identical reads from independent cDNA molecules are expected at a higher level than in non-strand-specific and non-DGE libraries. We do indeed observe higher sequence duplication for DGE than HTR (FIG. 2B). Non-DGE strand specific libraries have fuller transcript length coverage and show lower sequence duplication than DGE libraries resulting from higher sequence complexity (FIG. 10). Strand specific tomato SHO libraries made from similarly staged developing tomato leaves and *Arabidopsis* strand specific libraries (Hsu et al., 2013) downloaded from the Gene Expression Omnibus (Acession: GSE38879) made using a deoxy-Uracil (dU) marked strand specific method (Wang et al, 2011) were also assessed and possess similar rates of duplication to on another (FIG. 10). To remove differences in sequencing depth between samples as a factor in read duplication counts a random subsample of 1 million reads was used from each FASTQ file for duplication analysis.

Additionally, in 3-prime DGE libraries not all poly-A runs are removed by quality filtering. Homonucleotide "A" repeats make up the predominant duplicated sequences in DGE libraries, comprising ~0.3% of quality filtered reads. After quality-filtering, GC content and per base sequence content differ between DGE and HTR (FIG. 2C) with lower GC content in strand-specific DGE library reads. Whereas individual base compositions in non-strand-specific libraries (e.g., HTR libraries) should contain roughly equal amounts of G to C and A to T nucleotides, G/C and A/T ratios are unequal for the coding strand of mRNAs. The proportions of each nucleotide in the sense strand of annotated tomato coding sequences were 22.1% G, 18.5% C, 29.9% A, 29.4% T. This closely matches the observed proportions in the DGE sequences: 22.5% G, 15.2% C, 28.5% A, 33.8% T (FIG. 2D). Quality scores, sequence content and GC distribution show similar performance between SHO and dU library methods (FIG. 11).

C. Adapter and rRNA Contamination

Adapter contamination was higher in DGE libraries than in HTR (FIG. 3A) consisting of ~5% of reads in DGE compared with ~1% of reads in HTR. This may be due to the use of higher PEG concentrations in the bead washing step in the DGE protocol. This could increase bead binding of small products. Approximately 1% of reads from DGE libraries could be attributed to ribosomal contamination compared with 0.22% to 0.39% in HTR libraries (FIG. 3B) and approximately 3% in tomato libraries made with a commercial Illumina kit (Kumar et al., 2012). Increased rRNA in DGE compared to HTR is likely due to single step mRNA isolation compared to two stage mRNA re-isolation in the HTR process.

D. Read Mapping

To reliably compare DGE and HTR libraries we created a set of reference sequences consisting of the annotated tomato coding sequence plus an additional downstream portion corresponding to the genome sequence 3-prime to the stop codon. Plant 3-prime untranslated regions (3'-UTRs) are variable in length and average around 200 bp (Mignone et al., 2002) but many 3'-UTRs are not annotated. For the purpose of this study 500 bp of downstream genomic sequence was chosen to encompass most 3'-UTR sequences and appended to the annotated ITAG2.4 coding sequences (ITAGcds+500). An additional mapping reference was generated specifically for DGE libraries consisting of the 3-prime 500 bp of the coding sequence plus an additional 500 bp representing the 3'-UTR (ITAG500+500) to minimize the effect of mis-priming of the 3-prime polyT containing adapter onto any A-rich regions within coding sequences.

The proportion of reads mapping one or more times to the plus and minus strands of the ITAGcds+500 reference is higher in DGE (85-87%) than HTR (77-78%) (FIG. 3C) demonstrating that a large majority of reads in both methods originate from mRNAs.

E. DGE 3-Prime Selectivity

There is a strong selectivity of the DGE library protocol for the 3-prime portion of mRNA transcripts whereas reads derived from HTR are more evenly distributed across transcripts. (FIG. 12). Although the ITAG500+500 reference sequences are, on average, 608 bp shorter than the ITAGcds+500 reference sequences, more DGE reads map uniquely and strand-specifically to the ITAG500+500 reference (78% to 81%) than the HTR reads mapping uniquely to the ITAGcds+500 reference (73% to 78%).

F. Strand-Specificity

To evaluate strand-specificity of the DGE libraries, reads were mapped to tomato coding sequences only (FIG. 3D) to exclude reads mapping to overlapping UTR regions. Approximately 99% of mapped reads in DGE libraries and 50% of mapped reads in HTR libraries localize to the sense strand, indicating a very high degree of strand-specificity for the DGE libraries. Directional information of the cDNA molecule is preserved because only the cDNA strand of the RNA-cDNA duplex can serve as a template for Pol I. We have successfully produced libraries using this method with *E. coli* Pol I, Klenow fragment, and Klenow exo-(FIG. 7C) indicating the exonuclease activity of Pol I is not required for the process to work efficiently.

A large majority of uniquely mapped reads (95%) in the DGE libraries map to a region +/−500 bp of the annotated stop codons of ITAGcds+500 reference (Table 2), whereas HTR libraries show a more even distribution across the transcript (FIG. 4A). The DGE reads localize almost entirely to the 3-prime region of the transcript including downstream of the annotated stop codon, suggesting that only this interval is necessary for mapping DGE reads. HTR reads by comparison show a more even distribution but still bias toward sequence at the 3-prime of the transcript. Since not all coding sequences are 1 kb or longer, the read locations were also scaled to the portion of the coding sequence (FIG. 4B). HTR libraries still show a slight bias for sequences near the 3-prime end of the CDS. SHO libraries show similar transcript coverage to HTR although SHO coverage shows somewhat higher 5-prime transcript representation (FIG. 13).

TABLE 2

DGE read mapping location in ITAGcds + 500 reference with respect to the stop codon.

| Fraction of mapped reads | Region of reference sequence |
|---|---|
| >50% | −60 to +120 |
| >75% | −150 to +200 |
| >85% | −250 to +250 |
| >95% | −500 to +500 |

To ascertain the degree of sequence selection bias introduced by the adapter capture process, 20 nucleotides the adapter. The strand specificity of the DGE libraries also allows for unambiguous assignment of the transcript of origin for genes in which the terminator regions overlap (FIG. 14).

G. Detection of Gene Expression

Reads were analyzed from equally-sized subsets of pre-quality-filtered reads (Table 3). The number of transcripts with mapped reads is reduced in both DGE and HTR libraries when excluding non-uniquely-mapped reads. The limited span of the transcript incorporated into DGE libraries, in combination with retaining only uniquely mapped reads and strand specificity may reduce the false detection of transcripts where genomic locations of transcripts overlap and where coding sequences are highly conserved.

TABLE 3

Transcript detection for pre-quality-filtered subsets of 6.5M reads each for DGE and HTR.

| Combined sample | Initial reads | Passing QF | Non-uniquely mapping — Mapping to both strands — ITAGcds + 500 | | | | | | Uniquely mapping — Mapping to sense strand — ITAG500 + 500 | | |
|---|---|---|---|---|---|---|---|---|---|---|---|
| | | | Mapped | Percent mapped | Transcripts detected | Reads mapping | Percent QF reads mapped | Transcript with hits | Reads mapping | Percent QF reads mapped | Transcripts with hits |
| DGE-SAM | 6,500,000 | 5,255,791 | 4,449,163 | 85 | 23,348 | 4,252,370 | 81 | 21,618 | 4,113,253 | 78 | 20,922 |
| DGE-Leaf | 6,500,000 | 5,230,179 | 4,442,859 | 85 | 23,395 | 4,232,606 | 81 | 21,574 | 4,117,670 | 79 | 20,893 |
| HTR-SAM | 6,500,000 | 5,745,924 | 4,508,993 | 78 | 24,931 | 4,355,096 | 76 | 22,999 | | | |
| HTR-Leaf | 6,500,000 | 5,741,410 | 4,447,320 | 77 | 24,526 | 4,280,954 | 75 | 22,627 | | | | upstream of the first mapped nucleotide for each read was extracted from the FASTA mapping reference for base composition (FIG. 4C) and information content (FIG. 14). Positions −8 through −1 correspond to the cDNA region annealed to the 8 bp single stranded portion of the adapter responsible for breath capture of the DNA-RNA duplex. Positions −20 through −9 correspond to the "shielded" double stranded portion of the adapter containing the Illumina TruSeq PE1 sequence. Despite the presence of the shielding (blocking) oligonucleotide, the positions approaching the −9 map location corresponding to the last few bases of the adapter show some sequence bias near the end of the double stranded region (FIGS. 15A-15D). This suggests that duplex breathing of the adapter at the capturing end transiently exposes the first few internal bases, allowing for increased interaction with cDNA sequences with some complementarity. While the degree and range of this sequence selection bias is significantly improved over earlier versions of this protocol utilizing un-shielded single stranded adapters, it may still be further improved by converting the first base of the random 8-mer into an extended double-stranded shield region. Retention of the template mRNA strand prevents access to the interior portions of the cDNA. This restricts the interactions of the adapter to the terminal portion of the cDNA, which provides control of library size through mRNA fragmentation and limits the effects of sequence specific secondary structures. Increasing magnesium concentration in the breath capture reaction to 20 mM improves library yield (FIG. 7B) potentially through increased strength of base-pair interactions between the cDNA strand and the capturing nucleotides of Non-uniquely mapping reads mapping to both strands of ITAGcds+500 reference, uniquely mapping reads mapping to both strands of ITAGcds+500 and uniquely mapping reads mapping to sense strand of ITAG500+500 reference.

Correlation between replicates is higher for DGE than HTR samples (FIGS. 5A-5D and Table 5). R-squared values for all pairwise comparisons of Log 2-transformed expression showed higher correlation between DGE (SAM 0.96, Leaf 0.95) replicates than HTR (SAM 0.91, Leaf 0.93). These values are also similar for DGE and *Arabidopsis* dU libraries (0.96) as well as between HTR and SHO (0.92). Variation between DGE and HTR experimental samples was also assessed using multidimensional scaling (MDS) (FIG. 6A). Both DGE and HTR samples cluster by tissue type although distance between SAM and Leaf clusters is greater along dimension 2 for DGE libraries suggesting a high power of discrimination between tissues by gene expression. Differential gene expression calls between DGE and HTR show a high degree of overlap (Table 4). We found very strong correlation ($r_s$=0.92) between the $\log_2$ fold-change of genes that are differentially regulated (FDR<0.05) in SAM vs. leaf samples for both library preparation methods. The correlation remains very strong when considering genes differentially regulated for only the DGE method ($r_s$=0.87; orange in FIG. 6B) or only the HTR method ($r_s$=0.87; blue in FIG. 6B).

TABLE 4

| | DGE Total | HTR total | DGE only | Both | HTR only |
|---|---|---|---|---|---|
| Differential gene expression calls for DGE and HTR library samples. | | | | | |
| FDR 0.05 | | | | | |
| Up (S vs. L) | 2534 | 1386 | 1630 | 904 | 482 |
| Down (S vs. L) | 3014 | 1751 | 1615 | 1399 | 352 |
| FDR 0.01 | | | | | |
| Up (S vs. L) | 1766 | 722 | 1251 | 515 | 207 |
| Up (S vs. L) | 2376 | 1128 | 1413 | 963 | 165 |

To compare within and across method differential expression results, we divided the samples into ten groups of two replicates. The ten sample groups were: 2 HTR leaf, 2 HTR SAM, 3 DGE leaf, and 3 DGE SAM. Within each library preparation method, we performed differential gene expression analysis for all combinations of leaf×SAM. This resulted in 4 comparisons for HTR and 9 for DGE. With these, we were able to calculate Spearman's Ranked Correlation Coefficient for all combinations of leaf-SAM differentially expressed genes within (45 for DGE and 6 for HTR) and between (36 for DGE vs. HTR) each library preparation method (FIG. 12). We found that although the fold-change of differentially regulated genes is less correlated when comparing between library preparation methods than within, both between- and within-method comparisons show very strongly correlation.

H. Cost

We sought to minimize library prep cost and complexity by developing a protocol that uses mostly unmodified oligonucleotides and minimizes handling, steps, and reagents. The cost of isolating mRNA and making strand-specific libraries with this method is extraordinarily low, with magnetic bead, dNTP, and enzyme costs totaling $2.96/sample including mRNA isolation or $1.98 if making libraries from mRNA. Even allowing for the additional cost of consumables, chemical reagents and an extra 10% volume for reaction master mixes, this method provides a 20-40 fold cost reduction over available commercial strand-specific methods (e.g., NEBNext® Ultra™ Directional RNA Library Prep Kit for Illumina® 96 reactions Cat. #E7420L, SureSelect Strand Specific RNA-Seq Library Preparation kit for 96 samples reactions Cat. #G9691A).

I. Protocol Development

We had initially set out to modify a template switching protocol, but ended up making a discovery that would enable us to create arguably the cheapest and fastest RNA-seq protocol to date. Our original goal was to try to use adapter-encoded index sequences together with barcode sequences within the primary reads to achieve extremely dense multiplexing of samples. The 5-prime adapters were designed as single-stranded molecules with a partial Illumina PET sequence followed by a 9-base-pair sequence (a 6 base pair barcode and 3 terminal guanines) to facilitate base-pairing with non-templated cytosines added to the cDNA by MMLV polymerase. The addition of adapter sequence to the cDNA was done in a second reaction using *E. coli* Polymerase I following a size-selection bead cleanup to avoid "background cDNA" composed of adapter concatamers.

Our initial libraries showed a highly heterogeneous enrichment of identical pooled test mRNA dependent on the barcode sequence contained in the adapter (FIG. 17), with significant visible banding due to massive overrepresentation of specific amplicons which vary with the adapter barcode sequence. Following trimming of the first 9 nucleotides from the Illumina reads, mapping to tomato transcripts, and clustering of samples unexpectedly showed grouping based on barcode sequence and not on sample type (FIG. 18). Additionally, in the first attempt libraries only a small numbers of transcripts accounted for the majority of read counts.

Further investigation of these unexpected results showed that, while cDNA libraries that could be sequenced on the Illumina platform were produced, the priming mechanism did not utilize template switching as originally envisioned. Sequence analysis of the transcript reference sequences located 5-prime to the first mapped nucleotide of the trimmed reads showed an extreme bias in the sequenced tomato transcripts for nucleotides matching the barcode sequence and "G" repeats (FIGS. 19-20) and further upstream sequences continued to include similarity to the PET sequence of the adapter. This indicated that base-pairing interactions between the terminal portion of the double-stranded cDNA and the barcode-containing portion of the adapter were selecting the transcripts that would be represented in the libraries.

Despite the rarity of any particular 9 base pair sequence in a given genome (one instance every 3.8e-06 bases), 74% of reads contained a perfect 9 base pair match to the barcode followed by 3 "G"s in the pre-trimmed portion of the read (FIG. 21). This showed that the dominant template for the sequencing reaction was the strand primed from 3-prime end of the adapter using the cDNA as a template. Consequently, the addition of non-templated "C"s by MMLV reverse transcriptase to the cDNA molecule likely blocked priming on the adapter oligonucleotide forcing the majority of sequenced molecules to originate from the second strand.

This suggested that there was a breathing effect in the double stranded template. We redesigned the 5-prime adapters to take advantage of this breath-capture effect and eliminate the sequence biases created by our early adapters. The portion of the adapter containing the Illumina PET sequence was shielded by annealing a complementary sequence oligonucleotide and the following 9 bases were replaced with variable length extensions of random mixed-base sequences, with extensions between 6 and 8 nucleotides outperforming shorter and longer variants. Adapter variants incorporating blocking groups at the 3-prime end of the random nucleotide extension performed extremely poorly indicating that priming from this strand was essential for library formation using this process.

Analysis of read coverage by base position in transcript (FIG. 22) shows that the Breath Adapter Directional sequencing (BrAD-Seq) method has increased representation of the 5-prime regions of transcript. This is of great use in genome annotation and medical diagnostics.

CONCLUSION

We have developed a rapid and inexpensive method for making strand-specific 3-prime DGE RNA-seq libraries from tissue in a multiplexed format. The entire process can be completed in a single working day. To our knowledge this is the first library construction process to utilize the terminal breathing of nucleic acid duplexes to selectively and directionally add adapter sequences. We have further developed the process to include modules allowing the creation of a variety of library types. We have also used the core DGE method on a number of species in addition to *S. lycopersicum* including *C. pentagona, S. pennellii, S. pimpinellifolium, S. neorickii* and *N. tobacum*. To date we have successfully used our DGE protocol to study differential gene expression in a number of studies relating to development and abiotic stress with good results. We have added and adapted modules to this core protocol for our own purposes and we provide those modules as well so that others can also use this protocol as the basis for a universal RNA and DNA-seq library protocol family. In the hope of helping to democratize NGS sequencing technologies we offer an inexpensive and easily implemented protocol for the preparation of NGS libraries. This study was published as Townsley et al., Frontiers in Plant Science, 2015, 6(366):1-11, doi:10.3389/fpls.2015.00366.

Koesterke, L., Piel, W. H., Grene, R., Noutsos, C., Gendler, K., Feng, X., Tang, C., Lent, M., Kim, S.-J., Kvilekval, K., Manjunath, B. S., Tannen, V., Stamatakis, A., Sanderson, M., Welch, S. M., Cranston, K. A., Soltis, P., Soltis, D., O'meara, B., Ane, C., Brutnell, T., Kleibenstein, D. J., White, J. W., Leebens-Mack, J., Donoghue, M. J., Spalding, E. P., Vision, T. J., Myers, C. R., Lowenthal, D., Enquist, B. J., Boyle, B., Akoglu, A., Andrews, G., Ram, S., Ware, D., Stein, L., and Stanzione, D. (2011). The iPlant collaborative: cyberinfrastructure for plant biology. Frontiers in Plant Science 2.

TABLE 5

R-squared values for all pairwise replicate sample comparisons log2 normalized read counts.

| Mean | HTR leaf | L_HTR_A4 | L_HTR_B5 | L_HTR_C6 | L_HTR_D7 |
|---|---|---|---|---|---|
| 0.9277 | L_HTR_A4 | | | | |
| | L_HTR_B5 | 0.9283 | | | |
| | L_HTR_C6 | 0.9307 | 0.9201 | | |
| | L_HTR_D7 | 0.9320 | 0.9229 | 0.9324 | |

| Mean | HTR SAM | S_HTR_A5 | S_HTR_A6 | S_HTR_B6 | S_HTR_B7 |
|---|---|---|---|---|---|
| 0.9064 | S_HTR_A5 | | | | |
| | S_HTR_A6 | 0.9111 | | | |
| | S_HTR_B6 | 0.9086 | 0.9293 | | |
| | S_HTR_B7 | 0.9209 | 0.8887 | 0.8797 | |

| Mean | DGE Leaf | L_DGE_A4 | L_DGE_B5 | L_DGE_C6 | L_DGE_D7 | L_DGE_E7 | L_DGE_E8 | L_DGE_F1 |
|---|---|---|---|---|---|---|---|---|
| 0.9523 | L_DGE_A4 | | | | | | | |
| | L_DGE_B5 | 0.9599 | | | | | | |
| | L_DGE_C6 | 0.9605 | 0.9600 | | | | | |
| | L_DGE_D7 | 0.9614 | 0.9603 | 0.9607 | | | | |
| | L_DGE_E7 | 0.9572 | 0.9553 | 0.9519 | 0.9581 | | | |
| | L_DGE_E8 | 0.9541 | 0.9541 | 0.9516 | 0.9578 | 0.9657 | | |
| | L_DGE_F1 | 0.9360 | 0.9328 | 0.9347 | 0.9405 | 0.9429 | 0.9433 | |

| Mean | DGE SAM | S_DGE_A5 | S_DGE_A6 | S_DGE_B7 | S_DGE_C7 | S_DGE_D8 | S_DGE_E1 | S_DGE_F2 |
|---|---|---|---|---|---|---|---|---|
| 0.9582 | S_DGE_A5 | | | | | | | |
| | S_DGE_A6 | 0.9591 | | | | | | |
| | S_DGE_B7 | 0.9564 | 0.9599 | | | | | |
| | S_DGE_C7 | 0.9567 | 0.9565 | 0.9518 | | | | |
| | S_DGE_D8 | 0.9588 | 0.9594 | 0.9524 | 0.9608 | | | |
| | S_DGE_E1 | 0.9564 | 0.9590 | 0.9522 | 0.9615 | 0.9631 | | |
| | S_DGE_F2 | 0.9575 | 0.9614 | 0.9557 | 0.9594 | 0.9617 | 0.9623 | |

| Mean | dU | dU_1 | dU_2 | dU_3 |
|---|---|---|---|---|
| 0.9564 | dU_1 | | | |
| | dU_2 | 0.9564 | | |
| | dU_3 | 0.9582 | 0.9545 | |

| Mean | SHO | SHO_1 | SHO_2 | SHO_3 |
|---|---|---|---|---|
| 0.92252 | SHO_1 | | | |
| | SHO_2 | 0.926926 | | |
| | SHO_3 | 0.920931 | 0.919703 | |

REFERENCES

Armour, C. D., Castle, J. C., Chen, R., Babak, T., Loerch, P., Jackson, S., Shah, J. K., Dey, J., Rohl, C. A., Johnson, J. M., and Raymond, C. K. (2009). Digital transcriptome profiling using selective hexamer priming for cDNA synthesis. Nature Methods 6, 647-U635.

Goff, S. A., Vaughn, M., Mckay, S., Lyons, E., Stapleton, A. E., Gessler, D., Matasci, N., Wang, L., Hanlon, M., Lenards, A., Muir, A., Merchant, N., Lowry, S., Mock, S., Helmke, M., Kubach, A., Narro, M., Hopkins, N., Micklos, D., Hilgert, U., Gonzales, M., Jordan, C., Skidmore, E., Dooley, R., Cazes, J., Mclay, R., Lu, Z., Pasternak, S., Hsu, P. Y., Devisetty, U. K., and Harmer, S. L. (2013). Accurate timekeeping is controlled by a cycling activator in Arabidopsis. Elife 2.

Koboldt, D. C., Steinberg, K. M., Larson, D. E., Wilson, R. K., and Mardis, E. R. (2013). The Next-Generation Sequencing Revolution and Its Impact on Genomics. Cell 155, 27-38.

Kumar, R., Ichihashi, Y., Kimura, S., Chitwood, D. H., Headland, L. R., Peng, J., Maloof, J. N., and Sinha, N. R. (2012). A high-throughput method for Illumina RNA-Seq library preparation. Frontiers in Plant Science 3.

Langmead, B., Trapnell, C., Pop, M., and Salzberg, S. L. (2009). Ultrafast and memory-efficient alignment of short DNA sequences to the human genome. Genome Biology 10.

Lister, R., O'malley, R. C., Tonti-Filippini, J., Gregory, B. D., Berry, C. C., Millar, A. H., and Ecker, J. R. (2008). Highly integrated single-base resolution maps of the epigenome in *Arabidopsis*. Cell 133, 523-536.

Meyer, M., and Kircher, M. (2010). Illumina sequencing library preparation for highly multiplexed target capture and sequencing. Cold Spring Harbor protocols 2010, pdb.prot5448-pdb.prot5448.

Mignone, F., Gissi, C., Liuni, S., and Pesole, G. (2002). Untranslated regions of mRNAs. Genome biology 3, REVIEWS0004-REVIEWS0004.

Parkhomchuk, D., Borodina, T., Amstislavskiy, V., Banaru, M., Hallen, L., Krobitsch, S., Lehrach, H., and Soldatov, A. (2009). Transcriptome analysis by strand-specific sequencing of complementary DNA. Nucleic Acids Research 37.

Regev, A., Levin, J. Z., and Yassour, M. (2012). Comprehensive comparative analysis of strand-specific RNA sequencing methods. ArrayExpress Archive.

Sémon, S. P.a.M. (2014). Transcriptomics of developing embryos and organs: A raising tool for evo-devo. Journal of Experimental Zoology.

Tang, F., Barbacioru, C., Nordman, E., Li, B., Xu, N., Bashkirov, V. I., Lao, K., and Surani, M. A. (2010). RNA-Seq analysis to capture the transcriptome landscape of a single cell. Nature Protocols 5, 516-535.

Von Hippel, P. H., Johnson, N. P., and Marcus, A. H. (2013). Fifty Years of DNA "Breathing": Reflections on Old and New Approaches. Biopolymers 99, 923-954.

Wang, L., Si, Y., Dedow, L. K., Shao, Y., Liu, P., and Brutnell, T. P. (2011). A Low-Cost Library Construction Protocol and Data Analysis Pipeline for Illumina-Based Strand-Specific Multiplex RNA-Seq. *Plos One* 6.

Zhu, Y. Y., Machleder, E. M., Chenchik, A., Li, R., and Siebert, P. D. (2001). Reverse transcriptase template switching: A SMART™ approach for full-length cDNA library construction. Biotechniques 30, 892-897.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

```
INFORMAL SEQUENCE LISTING
                              SEQ ID NO: 1
Synthetic oligonucleotide
5'-CCTACACGACGCTCTTCCGATCT SEQ ID NO: 2
Synthetic oligonucleotide
5'-AGATCGGAAGAGCGTCGTGTAGG SEQ ID NO: 3
Synthetic oligonucleotide
5'-CCTACACGACGCTCTTCCGATCTN₆₋₁₂, wherein N can be
any deoxyribonucleotide SEQ ID NO: 4
Synthetic oligonucleotide
5'-CCTACACGACGCTCTTCCGATCTNNNNNNN
```

26

```
-continued
                              SEQ ID NO: 5
Synthetic oligonucleotide
5'-CCTACACGACGCTCTTCCGATCTNNNNNNNN SEQ ID NO: 6
Synthetic oligonucleotide
5'-CCTACACGACGCTCTTCCGATCTNNNNNNNNN SEQ ID NO: 7
Synthetic oligonucleotide
5'-CCTACACGACGCTCTTCCGATCTNNNNNNNNNN SEQ ID NO: 8
Synthetic oligonucleotide
5'-CCTACACGACGCTCTTCCGATCTNNNNNNNNNNN SEQ ID NO: 9
Synthetic oligonucleotide
5'-CCTACACGACGCTCTTCCGATCTNNNNNNNNNNNN SEQ ID NO: 10
Synthetic oligonucleotide
5'-CCTACACGACGCTCTTCCGATCTNNNNNNNNNNNNN SEQ ID NO: 11
Synthetic oligonucleotide
5'-bio- ACAGGACATTCGTCGCTTCCTTTTTTTTTTTTTTTTTTTT SEQ ID NO: 12
Synthetic oligonucleotide
5'-GTGACTGGAGTTCAGACGTGTGCTCTTCCGATCTTTTTTTTTTTTTT
TTTTTTTV SEQ ID NO: 13
Synthetic oligonucleotide
5'-GTGACTGGAGTTCAGACGTGTGCTCTTCCGATCTNNNNNNNNN-3'

SEQ ID NO: 14
Synthetic oligonucleotide
5'-CAAGCAGAAGACGGCATACGAGATNNNNNNNNNGTGACTGGAGTTCA
GACGTGTGCTCTTCCGAT SEQ ID NO: 15
Synthetic oligonucleotide
5'-AATGATACGGCGACCACCGAGATCTACACTCTTTCCCTACACGACG
CTCTTCCGATCT SEQ ID NO: 16
Synthetic oligonucleotide
5'-AATGATACGGCGACCACCGA SEQ ID NO: 17
Synthetic oligonucleotide
5'-CAAGCAGAAGACGGCATACGA SEQ ID NO: 18
Synthetic oligonucleotide
5'-AAAAAAAAAAAAAAA SEQ ID NO: 19
Synthetic oligonucleotide
5'-TTTTTTTTTTTTTTTTTV SEQ ID NO: 20
Synthetic oligonucleotide
5'-NNNNNNNNN SEQ ID NO: 21
Synthetic oligonucleotide
5'-NNNNNNNNN
```

What is claimed is:

1. A method of generating a strand-specific DNA molecule from double stranded nucleic acid, the method comprising:

providing a double-stranded nucleic acid duplex comprising a first strand and a second strand;

without removal of the first strand or the second strand, annealing a partially double stranded oligonucleotide 5' adapter to the 3' end of the first strand in the duplex, wherein the 5' adapter comprises:

(i) a first strand capturing oligonucleotide comprising at least 20 nucleotides and a 3' overhang comprising about 6-12 consecutive random nucleotides that anneal to the 3' end of the first strand; and (ii) a second strand blocking oligonucleotide comprising at least 20 nucleotides complementary to at least a portion of the first strand capturing oligonucleotide; and generating the strand specific DNA molecule by extending the first strand capturing oligonucleotide of the 5' adapter using a DNA polymerase or a fragment thereof to generate a DNA strand complementary to the first strand.

2. The method of claim 1, wherein the double-stranded nucleic acid duplex is a double-stranded DNA.

3. The method of claim 1, wherein the providing comprises isolating the double-stranded nucleic acid duplex from a biological sample.

4. The method of claim 3, wherein the biological sample is an animal tissue sample.

5. The method of claim 3, wherein the biological sample is a plant tissue sample.

6. The method of claim 1, wherein the providing comprises isolating a single-stranded DNA or RNA from a biological sample and converting the single-stranded DNA or RNA into the double-stranded nucleic acid duplex with a polymerase.

7. The method of claim 1, further comprising amplifying the second strand using a primer complementary to the second strand blocking oligonucleotide.

8. The method of claim 7, wherein amplifying comprises polymerase chain reaction.

9. The method of claim 1, further comprising determining the sequence of the amplified second strand.

10. The method of claim 1, wherein the DNA polymerase or fragment thereof is DNA polymerase I.

11. The method of claim 1, wherein the DNA polymerase or fragment thereof is Klenow fragment.

12. The method of claim 1, wherein the second strand blocking oligonucleotide of the 5' adapter is 5' phosphorylated.

13. The method of claim 12, wherein the DNA polymerase is a Klenow fragment and a ligase.

* * * * *